United States Patent
McBride et al.

(10) Patent No.: US 9,592,104 B2
(45) Date of Patent: *Mar. 14, 2017

(54) POLYAXIAL DENTAL IMPLANT SYSTEM

(71) Applicant: JBSG Management LLC, Santa Ana, CA (US)

(72) Inventors: Jim McBride, Corona, CA (US); Gonzalo Covarrubias, San Juan Capistrano, CA (US); Souhail Toubia, San Juan Capistrano, CA (US); Bradford Staph, Dana Point, CA (US)

(73) Assignee: JBSG MANAGEMENT LLC, Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,630

(22) Filed: Jul. 13, 2015

(65) Prior Publication Data

US 2015/0313691 A1    Nov. 5, 2015

Related U.S. Application Data

(63) Continuation of application No. 14/191,363, filed on Feb. 26, 2014, now Pat. No. 9,078,719, which is a
(Continued)

(51) Int. Cl.
*A61C 8/00* (2006.01)

(52) U.S. Cl.
CPC ............ *A61C 8/0053* (2013.01); *A61C 8/006* (2013.01); *A61C 8/008* (2013.01); *A61C 8/0022* (2013.01); *A61C 8/0074* (2013.01); *A61C 8/0089* (2013.01)

(58) Field of Classification Search
CPC ...... A61C 8/0053; A61C 8/0054; A61C 8/066
See application file for complete search history.

(56) References Cited

U.S. PATENT DOCUMENTS

| | | | |
|---|---|---|---|
| 3,732,621 A | 5/1973 | Bostrom | |
| 4,431,416 A | 2/1984 | Niznick | |

(Continued)

FOREIGN PATENT DOCUMENTS

| | | |
|---|---|---|
| FR | 2766354 A1 | 1/1999 |
| JP | S 63-125251 A | 5/1988 |

(Continued)

OTHER PUBLICATIONS

"Locate a Better Prosthetic Option with GPS" <www.implantdirect.com/newsletters/2012/ai.sub.--mail.htm>, visited Jul. 11, 2012.

*Primary Examiner* — Ralph Lewis
(74) *Attorney, Agent, or Firm* — Nathan S. Smith; McDermott Will & Emery LLP

(57) ABSTRACT

A dental implant system can include an upper implant body coupled to a lower body with a cavity between the upper and lower implant bodies. The system can further include an anchor at least partially disposed within the cavity. The system can also include an abutment that couples to the anchor and serves as a mounting area for a crown. The anchor can be rotatable and swivelable, allowing the lower implant body to be implanted at an angle in bone while permitting the crown to be positioned in a natural tooth orientation.

36 Claims, 20 Drawing Sheets

Related U.S. Application Data continuation of application No. 13/447,121, filed on Apr. 13, 2012, now Pat. No. 8,684,733.

(60) Provisional application No. 61/476,230, filed on Apr. 15, 2011, provisional application No. 61/487,591, filed on May 18, 2011, provisional application No. 61/512,366, filed on Jul. 27, 2011, provisional application No. 61/545,061, filed on Oct. 7, 2011.

(56) References Cited

U.S. PATENT DOCUMENTS

| | | | |
|---|---|---|---|
| 4,645,453 A | 2/1987 | Niznick | |
| 4,713,004 A | 12/1987 | Linkow et al. | |
| 4,932,868 A | 6/1990 | Linkow et al. | |
| 5,007,835 A | 4/1991 | Valen | |
| 5,071,350 A | 12/1991 | Niznick | |
| 5,302,125 A | 4/1994 | Kownacki et al. | |
| 5,564,922 A | 10/1996 | Rosa et al. | |
| 5,622,500 A | 4/1997 | Niznick | |
| 6,287,115 B1 | 9/2001 | Lustig et al. | |
| 6,843,653 B2 | 1/2005 | Carlton | |
| 8,684,733 B2 * | 4/2014 | McBride | A61C 8/0053 433/173 |
| 9,078,719 B2 * | 7/2015 | McBride | A61C 8/0053 |
| 2005/0042573 A1 | 2/2005 | Lustig et al. | |
| 2006/0024644 A1 | 2/2006 | Cohen | |
| 2009/0202962 A1 | 8/2009 | Xam-Mar Mangrane | |
| 2009/0246733 A1 | 10/2009 | Auderset et al. | |
| 2010/0036427 A1 | 2/2010 | Winslow et al. | |

FOREIGN PATENT DOCUMENTS

| | | |
|---|---|---|
| JP | 2005-528164 A | 9/2005 |
| JP | 2010-521265 A | 6/2010 |
| WO | WO-2014/106761 A2 | 7/2014 |

* cited by examiner

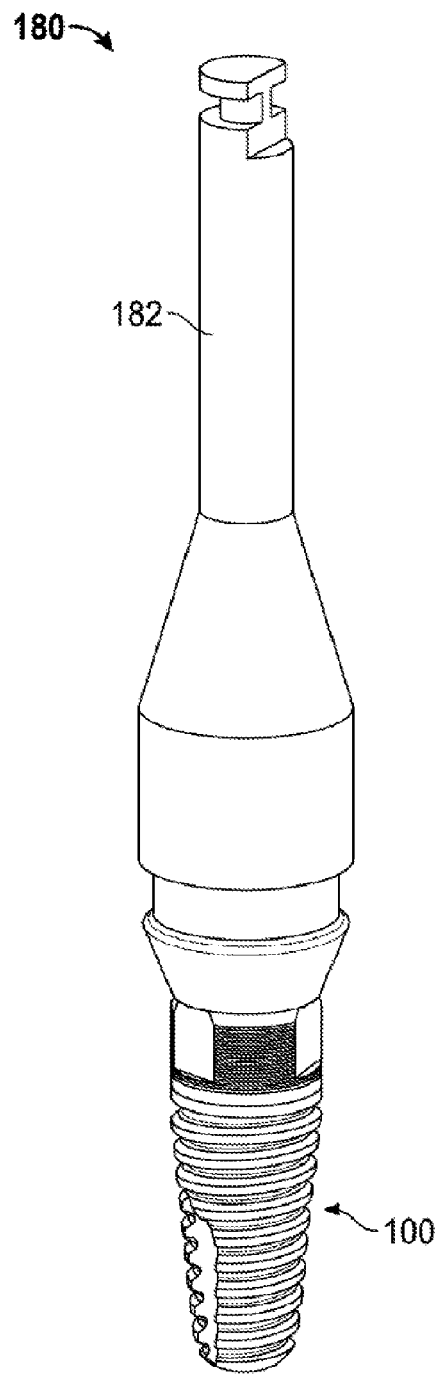
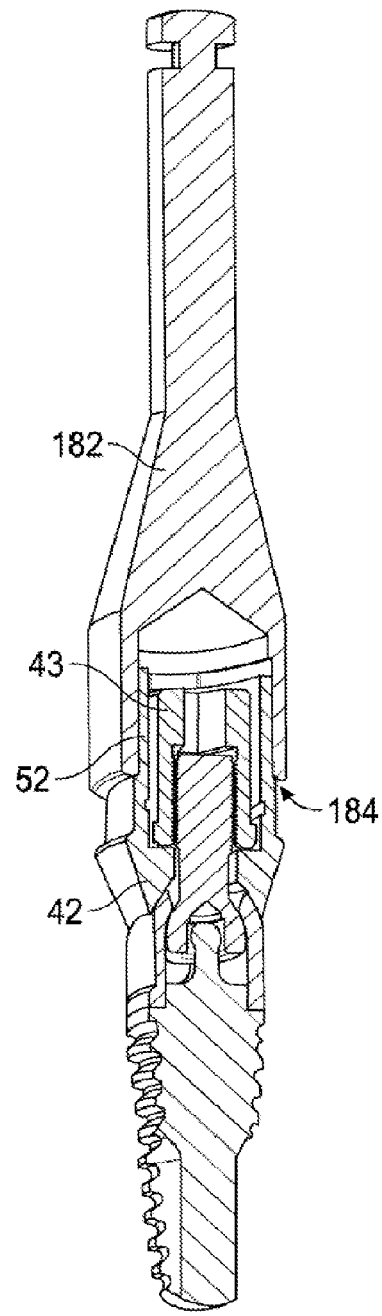
FIG. 18A
FIG. 18B

POLYAXIAL DENTAL IMPLANT SYSTEM

RELATED APPLICATIONS

This application is a continuation of U.S. patent application Ser. No. 14/191,363, filed on Feb. 26, 2014, which is a continuation of U.S. patent application Ser. No. 13/447,121, filed on Apr. 13, 2012, now U.S. Pat. No. 8,684,733, which claims the priority benefit of U.S. Provisional Applications No. 61/476,230, filed on Apr. 15, 2011, No. 61/487,591, filed on May 18, 2011, No. 61/512,366, filed on Jul. 27, 2011, and No. 61/545,061, filed on Oct. 7, 2011, all of which are hereby incorporated by reference in their entirety.

BACKGROUND

The subject technology generally relates to dental implants.

Implant dentistry involves the restoration of one or more teeth in a patient's mouth using artificial components. Such artificial components typically include an implant body, an abutment, and a crown. The completed assembly is referred to as a dental implant.

The implant body is the part of the dental implant that provides the anchor or foundation for the restoration. This part is fixed in the jaw bone, and can be threaded or non-threaded. Bone tissue tends to grow around the implant body and thus the jaw bone is strengthened. Commercially available implant bodies are typically made of either commercially pure titanium or a titanium alloy and, depending on the need, may be coated with hydroxyapatite to promote osseointegration. The abutment is the portion of the dental implant that attaches to the implant body and extends above the gumline and provides internal support to the artificial crown. The crown is the topmost part of the restoration and is the part that is visible in the mouth. Crowns for dental implants are similar to crowns applied over natural teeth and are usually made of metal or porcelain or a mixture of the two. FIGS. 1 and 2 illustrate two examples of existing dental implants.

Temporary components used during the implantation procedure include a healing screw and a healing cap. The healing screw is used after the implant body is initially placed while the soft tissue over the implant body is healing. The healing screw facilitates the suturing of the soft tissue and also prevents the growth of tissue over the edge of the implant. A healing cap is a dome-shaped cap that projects through the soft tissue into the oral cavity and further guide the growth of gum tissues around the implant body.

Generally, the process for restoring a tooth is carried out in four steps—diagnosis, implantation, attachment of the abutment, and attachment of the crown. During the diagnosis in Step 1, an X-ray image is typically taken of the patient's head to determine the shape and density of the bone structure of the jaw. In certain circumstances, a CAT scan may be required to provide more detailed information about the bone and the location of structures such as sinuses.

Step 2 involves implanting the dental implant into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant to be implanted. Then, the dental implant is inserted into the hole in the jawbone, typically by screwing, although other techniques are known for introducing the implant in the jawbone.

The implant itself is typically fabricated from pure titanium or a titanium alloy. Such materials are known to produce osseointegration of the fixture with the patient's jawbone. Existing dental implant typically include a hollow threaded bore through at least a portion of its body and extending out through its proximal end which is exposed through the crestal bone for receiving and supporting the final tooth prosthesis and/or various intermediate components or attachments.

After the implant is initially installed in the jawbone, a temporary healing screw is secured over the exposed proximal end in order to seal the internal bore. The patient's gums are then sutured over the implant body and screw to allow the implant site to heal and to allow desired osseointegration to occur. Complete osseointegration typically takes anywhere from four to ten months.

Step 3 is shown in FIG. 3A. The surgeon reassesses the implant fixture by making an incision through the patient's gum tissues. The healing screw is then removed, exposing the proximal end of the implant, and the abutment is attached to the implant body. Typically, an impression is then taken of the patient's mouth to accurately record the position and orientation of the implant and abutment within the mouth. This impression is used to create a plaster model or analogue of the mouth and/or the implant site and provides the information needed to fabricate the prosthetic replacement tooth and any required intermediate prosthetic components. Step 3 is typically completed by attaching a healing cap to the abutment to control the healing and growth of the patient's gum tissue around the implant site.

Between step 3 and step 4, a crown is fabricated from the plaster model created in step 3. Step 4 in the restorative process includes removing the temporary healing cap and attaching the crown to the abutment as shown in FIG. 3B.

SUMMARY

One limitation of current dental implants is that the implant body is aligned vertically, i.e., substantially perpendicularly, under, i.e. deep to, the tooth being replaced. In certain patients, especially a patient with osteoporosis, the bone structure and density immediately under the location of the tooth to be replaced may not be sufficient to provide adequate attachment to the implant body. In such a situation, it would desirable to be able to angle the implant body relative to a vertical line at the location of the tooth to be replaced.

Another limitation of current dental implants is that the abutment projects from the gum sufficient that a healing cap is often necessary to guide the healing of the gum around the abutment. The healing cap may be intrusive and present an opportunity for the accumulation of food and plaque that may interfere with proper healing. It would be desirable to avoid having to place an external healing cap over the abutment while providing a temporary element through the gum that would allow the gum to heal in this area.

Various exemplary embodiments of a dental implant system that addresses the above limitations are disclosed herein. The subject technology is illustrated, for example, according to various aspects described below. Various examples of aspects of the subject technology are described as numbered independent and dependent clauses (1, 2, 3, etc.) for convenience. These are provided as examples and do not limit the subject technology. It is noted that the features of any of the dependent clauses may be combined alone or in any combination into any of the independent claims or combined with other dependent claims so as to describe a particular embodiment.

Clause 1. A dental implant system comprising: a lower implant body configured to be implanted in bone; an upper implant body configured to couple to the lower implant body, thereby forming a cavity between the upper and lower implant bodies, the upper implant body comprising an opening to the cavity; and a rotatable, swivelable anchor comprising: a base disposed at least partially within the cavity, the base comprising a first substantially spherical surface; and a shaft coupled to the base and extending through the opening.

Clause 2. The dental implant system of clause 1, wherein the lower implant body is configured to sustain an insertion torque of at least 20 N·cm.

Clause 3. The dental implant system of clause 1, wherein the upper implant body further comprises an internal surface configured such that the first substantially spherical surface is at least partially in contact with the internal surface when the upper and lower implant bodies are coupled together with the base of the anchor disposed within the cavity.

Clause 4. The dental implant system of clause 3, wherein the internal surface comprises a second substantially spherical surface.

Clause 5. The dental implant system of clause 4, wherein the opening passes through the second substantially spherical surface.

Clause 6. The dental implant system of clause 1, wherein: the lower implant body comprises an anti-rotation post configured to project into the cavity when the upper and lower implant bodies are coupled together; and the base further comprises an anti-rotation cavity configured to engage the anti-rotation post when the base of the anchor is disposed within the cavity; and the anti-rotation post and anti-rotation cavity are configured to resist rotation of the anchor about a centerline of the lower implant body while allowing rotation of the anchor about axes perpendicular to the centerline.

Clause 7. The dental implant system of clause 6, wherein: the anti-rotation post comprises a hex ball; and the anti-rotation cavity comprises a hex pocket.

Clause 8. The dental implant system of clause 1, further comprising an abutment configured to couple to the shaft of the anchor.

Clause 9. The dental implant system of clause 8, wherein: the upper implant body further comprises an external third substantially spherical surface; and the abutment comprises a fourth substantially spherical surface configured such that the fourth substantially spherical surface is at least partially in contact with the third substantially spherical surface when the upper and lower implant bodies are coupled together with the base of the anchor disposed within the cavity and the abutment coupled to the shaft of the anchor.

Clause 10. The dental implant system of clause 8, wherein: the shaft of the anchor comprises threads; and the abutment comprises a nut configured to threadingly couple to the shaft of the anchor and thereby secure the abutment in a fixed orientation relative to the upper implant body.

Clause 11. The dental implant system of clause 10, wherein the nut is captive within the abutment.

Clause 12. The dental implant system of clause 1, wherein: the lower implant body comprises a first threaded portion; the upper implant body comprises a second threaded portion configured to be threadingly coupled to the first threaded portion; and the dental implant system further comprises a healing cover configured to be removably coupled to the first threaded portion.

Clause 13. The dental implant system of clause 1, wherein the upper and lower implant bodies are configured to be welded together.

Clause 14. The dental implant system of clause 1, further comprising an installation tool configured to be removably coupled to the upper implant body and apply a torque about the centerline of the lower implant body.

Clause 15. The dental implant system of clause 14, wherein the installation tool is further configured to be removably coupled to the shaft of the anchor.

Clause 16. The dental implant system of clause 1, further comprising an installation tool configured to be removably coupled to the abutment and apply a torque about the centerline of the lower implant body.

Clause 17. A method of implanting a dental implant, the method comprising the steps of: implanting a dental implant system in a bone, the dental implant system comprising an externally threaded lower implant body configured to be implanted in bone, an upper implant body configured to couple to the lower implant body thereby forming a cavity between the upper and lower implant bodies, the upper implant body comprising an opening to the cavity, and a rotatable, swivelable anchor comprising a base disposed at least partially within the cavity, the base comprising a first substantially spherical surface, and a shaft coupled to the base and extending through the opening; and coupling an abutment to the shaft of the anchor.

Clause 18. The method of clause 17, further comprising the steps of: coupling a healing cap to the abutment; allowing time for gum tissue adjacent to the bone to heal; and removing the healing cap.

Clause 19. A method of implanting a dental implant, the method comprising the steps of: implanting a lower implant body through tissue into bone; placing an anchor in contact with the lower implant body, the anchor comprising a base that comprises a first substantially spherical surface and a shaft extending radially from the base; placing an upper implant body, having an opening, over the rotatable attachment such that the shaft extends through the hole; and coupling the upper implant body to the lower implant body.

Clause 20. The method of clause 19, further comprising the steps of: coupling a healing cover to the lower implant body; allowing time for the bone to couple to the lower implant body; and removing the healing cover from the lower implant body.

Clause 21. A dental implant system comprising: an externally threaded lower implant body configured to be implanted in bone and to sustain a torque of at least 20 Newton-centimeters (N·cm); an upper implant body configured to couple to the lower implant body, thereby forming a cavity between the upper and lower implant bodies, the upper implant body having an upper opening to the cavity; and a rotatable, swivelable attachment comprising: a substantially spherical member disposed within the cavity; and a shaft coupled to the substantially spherical member and extending from the member through the opening.

Clause 22. The dental implant system of clause 21, wherein the externally threaded body is configured to sustain an insertion torque of at least 30 N·cm.

Clause 23. The dental implant system of clause 22, wherein the externally threaded body is configured to sustain an insertion torque of at least 50 N·cm.

Clause 24. The dental implant system of clause 21, further comprising an abutment configured to couple to the shaft of the rotatable attachment and to a prosthetic tooth.

Clause 25. The dental implant system of clause 24, wherein the abutment comprises a captive nut configured to threadingly couple to the shaft of the rotatable attachment.

Clause 26. A dental implant system comprising: a lower implant body configured to be implanted in bone; an upper implant body coupled to the lower implant body to form a cavity between the upper and lower implant bodies, the upper implant body having an opening to the cavity; a polyaxial sphere disposed within the cavity and having a radial bore; and an abutment configured to couple to a prosthetic tooth and having an internal passage; and an attachment element that passes through the passage, into the radial bore, and couples to the sphere, securing the abutment to the upper implant body.

Clause 27. A method of implanting a dental implant, comprising: implanting a lower implant body in bone; placing a rotatable attachment, having a substantially spherical member and a shaft extending radially from the member, in contact with the lower implant body; placing an upper implant body, having an opening, over the rotatable attachment such that the shaft extends through the hole; and coupling the upper implant body to the lower implant body.

Clause 28. The method of clause 27, further comprising coupling an abutment to the shaft, the abutment configured to attach to a prosthetic tooth.

Clause 29. A method of implanting a dental implant, the method comprising the steps of: implanting a lower implant body in bone; placing a polyaxial sphere having a radial bore in contact with the lower implant body; placing an upper implant body, having an opening, over the polyaxial sphere; coupling the upper implant body to the lower implant body; and placing an abutment, having a passage therethrough, in contact with the upper implant body, the abutment configured to attach to a prosthetic tooth.

Clause 30. The method of clause 29, further comprising passing an attachment element through the passage, through the opening, and into the bore; and coupling the attachment element to the polyaxial sphere.

Clause 31. A dental implant system comprising: a lower implant configured to be implanted in bone, the lower implant comprising: an externally threaded body having a center axis, the body configured to sustain an insertion torque of at least 20 N·cm; and an internal ball coupled to the body; an upper implant coupled to the lower implant to form a cavity between the upper and lower implants, wherein the internal ball is disposed within the cavity, the upper implant having an opening to the cavity; a rotatable attachment comprising: a substantially spherical member disposed within the cavity between the upper and lower implants, the substantially spherical member comprising a shaped pocket configured to accept the internal ball, the internal ball and shaped pocket configured such that the internal ball has restricted rotation relative to the body about the center axis and can rotate relative to the body about axes perpendicular to the center axis; and a shaft coupled to, and extending from, the substantially spherical member through the opening.

Clause 32. The dental implant system of clause 31, wherein the externally threaded body is configured to sustain an insertion torque of at least 30 N·cm.

Clause 33. The dental implant system of clause 32, wherein the externally threaded body is configured to sustain an insertion torque of at least 50 N·cm.

Clause 34. The dental implant system of clause 31, further comprising an abutment configured to couple to the shaft of the rotatable attachment.

Clause 35. The dental implant system of clause 31, wherein: the lower implant and the upper implant are formed as a single unitary implant; and the opening to the cavity is formed in a configuration that allows the substantially spherical member of the rotatable attachment to be inserted through the opening into the cavity so as to engage the internal ball, after which the unitary implant is manipulated to modify the opening to a configuration that retains the substantially spherical member within the cavity.

Clause 36. A dental implant system comprising: a body configured to be partially implanted in bone, the body comprising: a cavity comprising an internal surface, a portion of the internal surface being substantially spherical; and an opening through the body and within the substantially spherical portion of the internal surface, the opening having a perimeter; and an anchor comprising: a base comprising a substantially spherical external surface, the base disposed within the cavity with the substantially spherical external surface of the base in sealing contact with the substantially spherical internal surface of the cavity at least along the perimeter of the opening; and a shaft coupled to the base and extending from the base through the opening of the body.

Clause 37. The dental implant system of clause 36, wherein: the body comprises a first anti-rotation feature with an axis; the first anti-rotation feature is disposed within the cavity of the body; and the base of the anchor comprises a second anti-rotation feature configured to cooperate with the first anti-rotation feature when the anchor is disposed within the cavity; the first and second anti-rotation features are configured to cooperatively resist rotation of the base relative to the body about the axis of the first anti rotation feature while allowing rotation of the base relative to the body about axes that are perpendicular to the axis of the first anti rotation feature.

Clause 38. The dental implant system of clause 37, wherein: the first anti-rotation feature comprises a post; the second anti-rotation feature comprises an anti rotation cavity; at least a portion of the post is disposed within the anti rotation cavity.

Clause 39. The dental implant system of clause 38, wherein: the post comprises a plurality of curved features arranged symmetrically about the axis; the anti-rotation cavity comprises a plurality of symmetrically arranged curved features; the curved features of the post are disposed within the curved features of the anti-rotation cavity.

Clause 40. The dental implant system of clause 39, wherein the post and cavity each comprise six substantially cylindrical features arranged in a hexagonal configuration.

Clause 41. The dental implant system of clause 36, wherein the body comprises: a lower body configured to be implanted in bone; and an upper body coupled to the lower body; wherein the upper body and lower body cooperate to form the cavity.

Clause 42. A dental implant tool comprising: a body having a cavity at a proximal end, the cavity configured to engage a dental implant that comprises: a cavity comprising an internal surface, a portion of the internal surface being substantially spherical; and an opening through the body and within the substantially spherical portion of the internal surface, the opening having a perimeter; and an anchor comprising: a base comprising a substantially spherical external surface, the base disposed within the cavity with the substantially spherical external surface of the base in sealing contact with the substantially spherical internal surface of the cavity at least along the perimeter of the opening; and a shaft coupled to the base and extending from the base through the opening of the body.

Clause 43. The dental implant tool of clause 42, wherein the body further comprises a torque feature at a distal end opposite the proximal end, the torque feature configured to engage a torque-applying tool.

Clause 44. The dental implant tool of clause 42, further comprising an attachment element that passes through the body from the distal end toward the proximal end, the attachment element configured to engage the anchor of the dental implant.

Clause 45. A dental implant tool comprising: a body having a cavity at a proximal end, the cavity configured to engage an abutment of a dental implant, the dental implant further comprising: a cavity comprising an internal surface, a portion of the internal surface being substantially spherical; and an opening through the body and within the substantially spherical portion of the internal surface, the opening having a perimeter; and an anchor comprising: a base comprising a substantially spherical external surface, the base disposed within the cavity with the substantially spherical external surface of the base in sealing contact with the substantially spherical internal surface of the cavity at least along the perimeter of the opening; and a shaft coupled to the base and extending from the base through the opening of the body.

Clause 46. The dental implant tool of clause 45, further comprising an implant nut disposed within the abutment, the implant nut configured to engage the shaft of the anchor.

Clause 47. A dental implant system comprising: a body configured to be partially implanted in bone, the body comprising: a cavity comprising an internal surface, a portion of the internal surface being substantially spherical; and an opening through the body and within the substantially spherical portion of the internal surface, the opening having a perimeter; and an anchor comprising: a base comprising a substantially spherical external surface, the base disposed within the cavity with the substantially spherical external surface of the base in sealing contact with the substantially spherical internal surface of the cavity at least along the perimeter of the opening; and a shaft coupled to the base and extending from the base through the opening of the body; an abutment comprising a generally cylindrical cavity with a bottom and a side wall, the bottom comprising an external surface having a portion that is substantially spherical, the abutment further comprising a hole through the bottom that is configured to fit over the portion of anchor shaft that extends through the opening in the body; and a nut disposed within the cavity of the abutment and configured to engage at least a portion of the anchor shaft that extends through the opening in the body.

Clause 48. The dental implant system of clause 47, further comprising a healing cap configured to snap onto an abutment and ride against the top of the abutment.

Clause 49. The dental implant system of clause 47, wherein the anchor further comprises an anti-rotation feature configured to cooperate with a mating feature of the base to resist rotation of the anchor about a center axis of the base.

Clause 50. A method of providing a replacement tooth to a patient, the method comprising the step of: implanting a positionable dental implant into a jaw bone of the patient in an approximate surface location of the tooth that is being replaced, wherein the positionable dental implant comprises a base and an abutment, wherein the base comprises a positionable anchor comprising an anti-rotation feature that cooperates with a mating feature of the base to resist rotation of the anchor about a center axis of the base and a shaft that projects through a hole in the base, and wherein the abutment is releasably secured to the shaft of the anchor.

Clause 51. The method of clause 49, further comprising the step of: securing a healing cap over the abutment with an interior surface of the healing cap in contact with a top surface of the abutment.

Clause 52. The method of clause 49, wherein the step of implanting the positionable dental implant comprises the step of: implanting the base into the jaw bone at an angle to a center axis of the tooth that is being replaced so the base is in contact with a strongest portion of the jaw bone that is within the reach of the implant from the surface location of the tooth that is being replaced.

Clause 53. The method of clause 50, wherein the step of implanting the positionable dental implant further comprises the step of: adjusting the position of the abutment so that a central axis of the abutment is generally parallel to the center axis of the tooth that is being replaced.

Clause 54. The method of clause 51, wherein the step of adjusting the position of the abutment comprises the steps of: loosening a nut that is disposed within a cavity of the abutment and configured to engage the shaft of the positionable anchor thereby securing the abutment to the base; repositioning the anchor so that the central axis of the abutment is generally parallel to the center axis of the tooth that is being replaced; and tightening the nut.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 18A-18B depict perspective and cross-section views, respectively, of a T4 tool according to certain aspects of this disclosure.

DETAILED DESCRIPTION

The following description discloses embodiments of a positionable dental implant and method of implantation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The method and system disclosed herein are presented in terms of a dental implant used to replace a tooth for a human being. It will be apparent to those of ordinary skill in the art that these systems and methods may be applied in other applications such as veterinary medicine. Nothing in this disclosure, unless specifically stated, should be interpreted as limiting the disclosed systems and methods to the specific examples used herein.

Within this disclosure, the term "substantially spherical" refers to a two- or three-dimensional contour that does not necessarily imply a perfectly spherical shape. Rather, substantially spherical structures described herein may be substantially or partially spherical in shape, have substantially circular or elliptical cross-sections, and/or have openings, indentations, defects, or aberrations in shape without departing from the substance of the subject technology.

Within this disclosure, the term "substantially spherical surface" means that the surface has a one of more portions that share a common substantially spherical contour. The surface may be continuous or have grooves or recesses such that portions of the surface share the contour but are not continuous. The term "substantially spherical surface" does not imply that the surface subtends all or any particular portion of a sphere.

Within this disclosure, the term "substantially embedded" means that a portion of one item is embedded within a second item sufficient to fulfill an intended purpose. In some aspects, a majority of the first item may be embedded in the second item. In some aspects, for example attachment, only enough of the first object required to provide adequate attachment to the second item is embedded in the second item. In some aspects, a portion of the first item may protrude from the second item.

Figure 1:
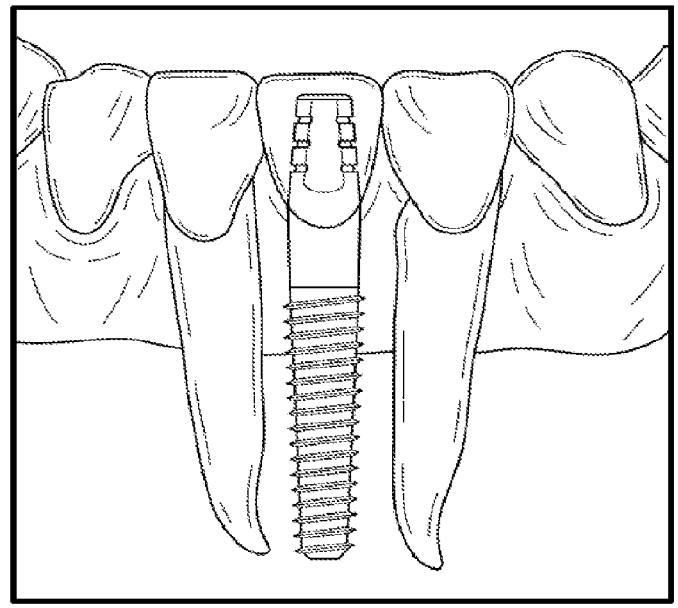
FIG. 1 is a cut-way illustration of an example of an existing dental implant.

FIG. 1 is a cut-way illustration of an example of an existing dental implant. The dental implant is shown in the position in which it would be implanted to replace the center tooth.

Figure 2:
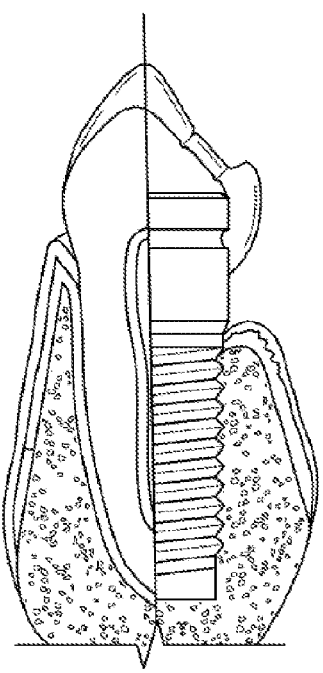
FIG. 2 is a cross-section of a natural tooth and a second example of an existing dental implant.

FIG. 2 is a cross-section of a natural tooth and a second example of an existing dental implant. The natural tooth structure is shown on the left and an example existing dental implant is shown on the right. This example dental implant has a threaded implant body and a cylindrical abutment that is screwed into a threaded recess (not visible) on the top of in the implant body. FIG. 2 also illustrates the position of the bone and gum around this example implant.

Figure 3A:
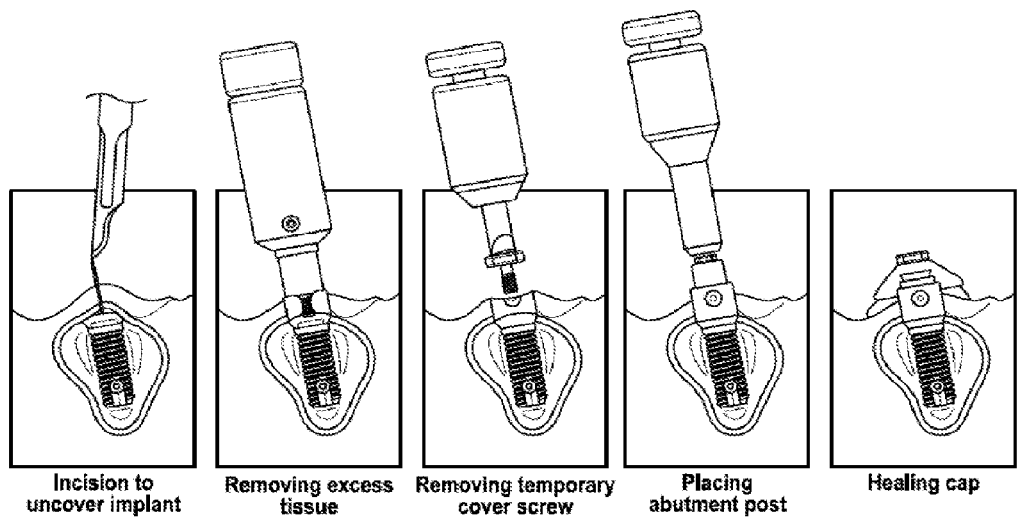
FIG. 3A illustrates a portion of the steps in a portion of an example existing implantation process.

FIG. 3A illustrates a portion of the steps in a portion of an example existing implantation process. The first picture is the state of the patient after the healing period has elapsed after the implant body was placed in the jaw. The second picture illustrates removal of the gum tissue overlying the implant using a tool, and the third picture is the removal of the temporary healing screw. The fourth picture illustrates installation of an abutment using a tool, and the fifth picture illustrates an installed healing cap over the abutment and gums.

Figure 3B:
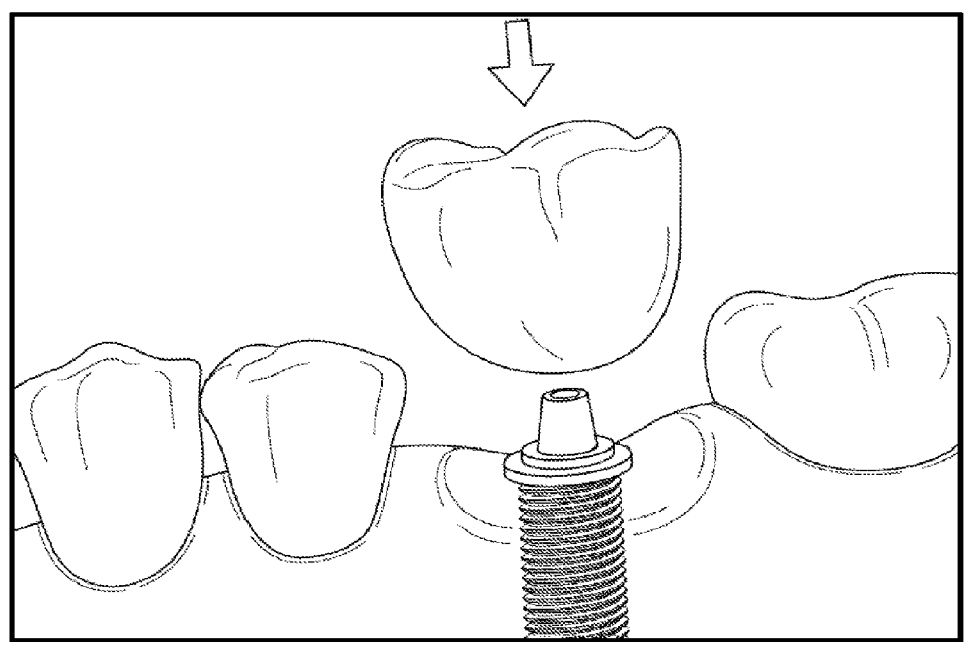
FIG. 3B illustrates a crown being attached to a abutment FIG. 1 in an example existing implantation process.

FIG. 3B illustrates a crown being attached to a abutment FIG. 1 in an example existing implantation process. In this example, the abutment is a simple pin and the crown has a matching recess (not visible) which is bonded to the pin.

Figure 4A:
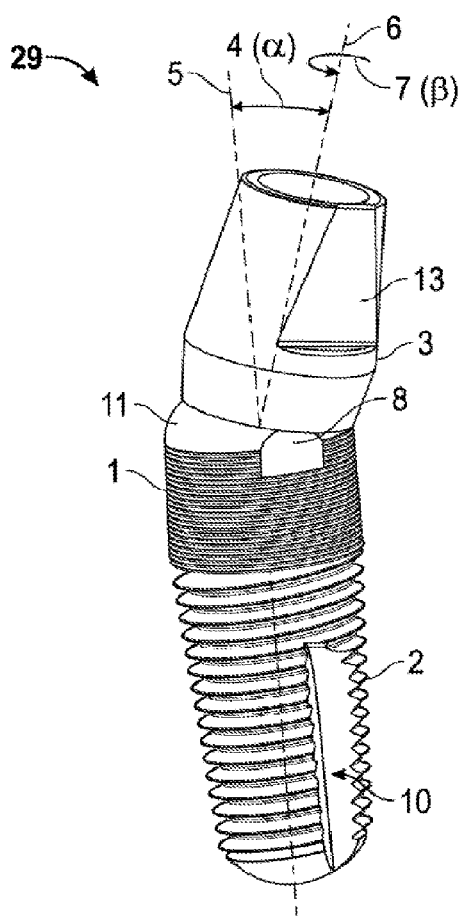
FIGS. 4A and 4B are perspective and cross-sectional views, respectively, of an exemplary positional dental implant according to certain aspects of this disclosure.
Figure 4B:
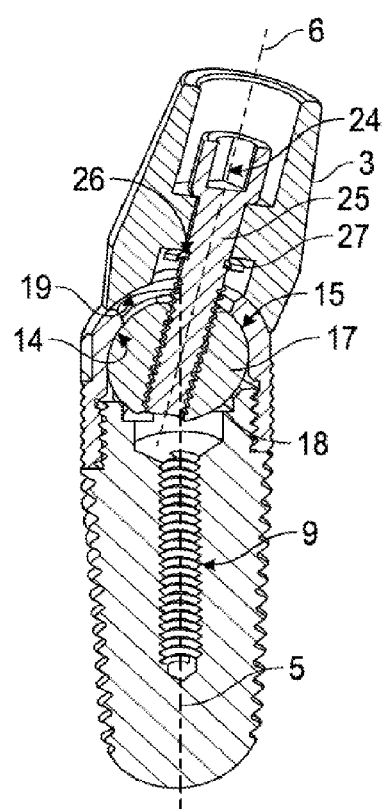

FIGS. 4A and 4B are perspective and cross-sectional views, respectively, of an exemplary positional dental implant according to certain aspects of this disclosure. The following features are identified in FIGS. 4A, 4B, 5A, and 5B.

| Ref. identifier | Feature |
| --- | --- |
| 1 | Upper implant |
| 2 | Lower implant |
| 3 | Abutment |
| 4 | Abutment inclination angle (alpha) |
| 5 | Lower implant centerline |
| 6 | Abutment centerline |
| 7 | Abutment rotation angle (beta) |
| 8 | upper implant scarf |
| 9 | threaded installation feature |
| 10 | Thread-cutting groove |
| 11 | third substantially spherical surface |
| 13 | Abutment scarf |
| 14 | second substantially spherical surface |
| 15 | first substantially spherical surface |
| 16 | Attachment interface |
| 17 | Polyaxial sphere |
| 18 | Flexure |
| 19 | fourth substantially spherical surface |
| 22 | attachment stop surfaces |
| 24 | Hexagonal recess |
| 25 | Fastener |

-continued

| Ref. identifier | Feature |
| --- | --- |
| 26 | Keeper groove |
| 27 | Keeper |
| 29 | positionable dental implant |

In certain embodiments, the lower implant body 2 is installed into the bone of a patient prior to assembly with the upper implant body 1. An installation tool (not shown in FIG. 4A) may be removable coupled to the lower implant body 2 and manipulated such that the lower implant body is inserted through the gum tissue of a patient and into the jaw bone. In certain embodiments, this installation includes the rotation of the lower implant body about axis 5 such that the external threads of the lower implant body 2 engage the bone. In certain embodiments, a thread-cutting groove 10 assists in cutting threads into the bone to assist in the implantation. In certain embodiments, a torque is applied to the lower implant body 2 to rotate the lower implant body as it is implanted into the bone. In certain embodiments, the lower implant body 2 is configured to withstand an installation torque of up to 20 newton-centimeters (N·cm). In certain embodiments, the lower implant body 2 is configured to withstand an installation torque of up to 30 N·cm. In certain embodiments, the lower implant body 2 is configured to withstand an installation torque of up to 50 N·cm.

In certain embodiments, the upper and lower implant bodies 1 and 2 are assembled prior to implantation of the lower implant body 2 into the bone of the patient. In certain embodiments, the upper and lower implant bodies 1 and 2 are coupled with threads. In certain embodiments, the upper implant body 1 is tightened onto the lower implant body 2 until the attachment stop surfaces 22 touch.

When the upper implant body 1 is coupled to the lower implant body 2, a flexure 18 is placed on the lower implant body 2, then a polyaxial sphere 17 is placed on the flexure 18 and the upper implant body 1 placed over the polyaxial sphere 17 and coupled to the power implant body 2. The flexure 18 applies a force to the polyaxial sphere 17 that places the first substantially spherical surface 15 in at least partial contact with the second substantially spherical surface 19. In this embodiment, the polyaxial sphere 17 is free to rotate away the axis 5, shown as an angle 4, also referred to as the 'alpha angle,' and rotate about the axis 6, also referred to as the 'beta angle,' which is also aligned with the attachment interface 16.

FIG. 4B illustrates an exemplary embodiment wherein abutment 3 is attached to the polyaxial sphere 17 with a fastener 25. In certain embodiments, the attachment 25 is a socket bolt having a hexagonal recess 24 that is used with a tool, such as a hex wrench (not shown in FIG. 4B, to tighten the fastener 25 to the polyaxial sphere 17.

Figure 5A:
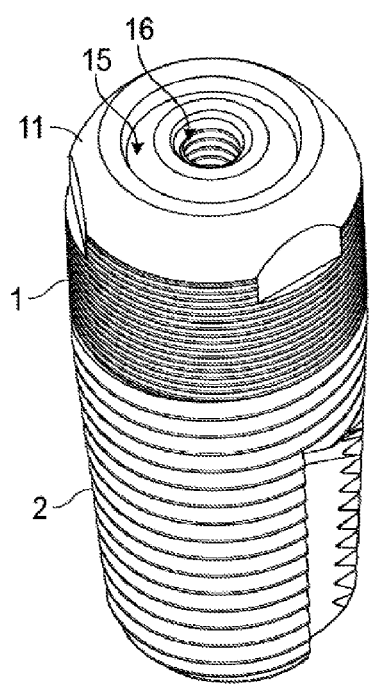
FIGS. 5A and 5B are perspective and cross-sectional views, respectively, of a portion of the positional dental implant of FIGS. 4A and 4B according to certain aspects of this disclosure.
Figure 5B:
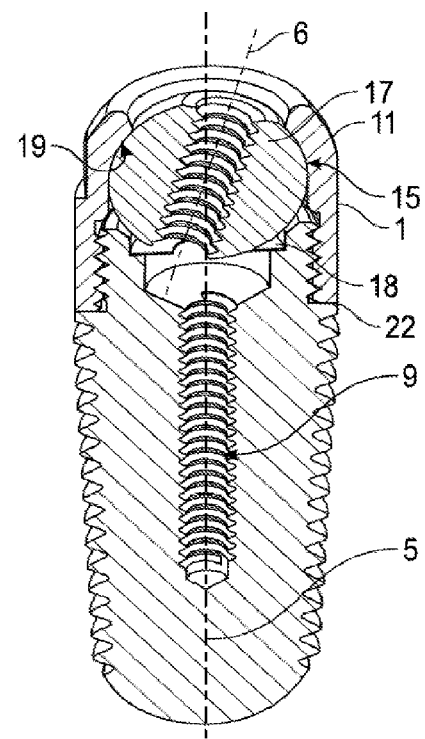

FIGS. 5A and 5B are perspective and cross-sectional views, respectively, of a portion of the positional dental implant 29 of FIGS. 4A and 4B according to certain aspects of this disclosure.

FIG. 5B illustrates a threaded installation feature 9 used, in certain embodiments, to enable attachment of an installation tool to the lower implant body 2. In certain embodiments, the attachment feature 16 is the same or larger than installation feature 9 such that a tool may pass through the attachment feature 16 to reach the installation feature 9 and thus allow installation of the assembled upper and lower implant bodies 1 and 2.

Figure 6A:
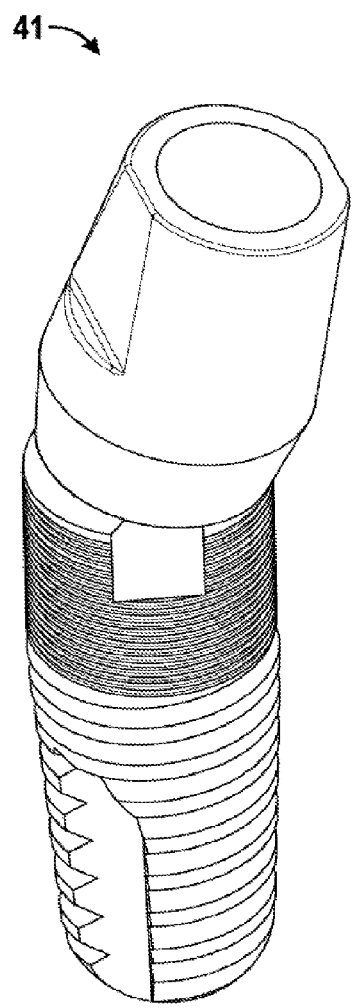
FIGS. 6A and 6B are perspective and cross-sectional views, respectively of another exemplary positional dental implant according to certain aspects of this disclosure.
Figure 6B:
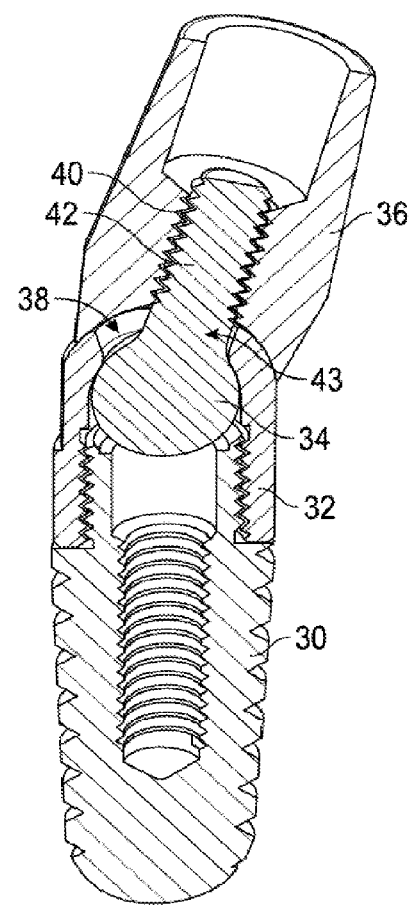

FIGS. 6A and 6B are perspective and cross-sectional views, respectively of another exemplary positional dental implant 41 according to certain aspects of this disclosure. The upper implant 32 and the lower implant 30 are similar to the upper and lower implants 1, 2 of FIGS. 4A and 4B. In this implant 41, a positionable anchor 43 comprises a base 34 that is captured between the upper and lower implants 32, 30 and a shaft 42 that is coupled to the base 34 and extends along a radial axis from the base 34. The anchor 43 is able to rotate and turn over a conical region defined by the movement of the shaft 42 within an opening 38 of the upper implant 32. In certain embodiments, the abutment 36 comprises a threaded bore 40 and the shaft 42 has a matching set of threads such that the abutment 36 may be screwed onto the threaded shaft 42. The angular position of the anchor 43 becomes fixed when the abutment 36 is tightened onto shaft 42.

Figure 7:
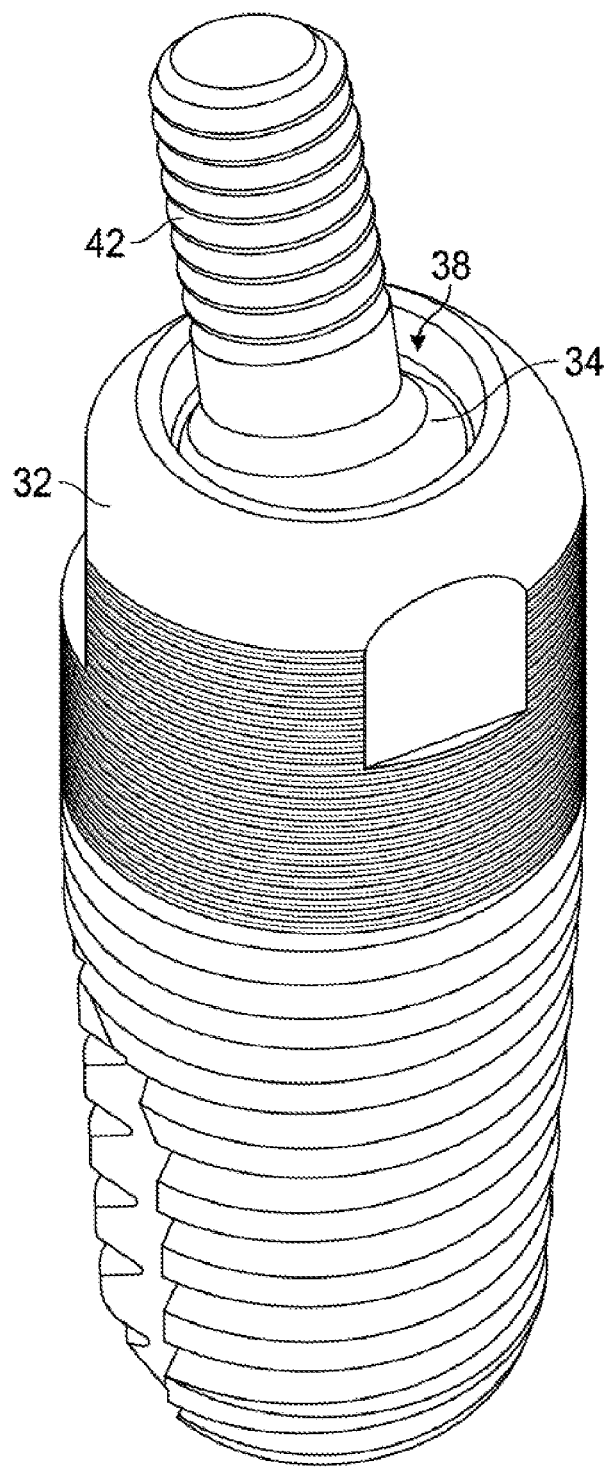
FIG. 7 is a perspective view of a portion of the positionable dental implant of FIGS. 6A and 6B according to certain aspects of this disclosure.

FIG. 7 is a perspective view of a portion of the positional dental implant of FIGS. 6A and 6B according to certain aspects of this disclosure. It can be seen how the shaft 42 can rotated as limited by the opening 38 of the upper implant 32.

Figure 8A:
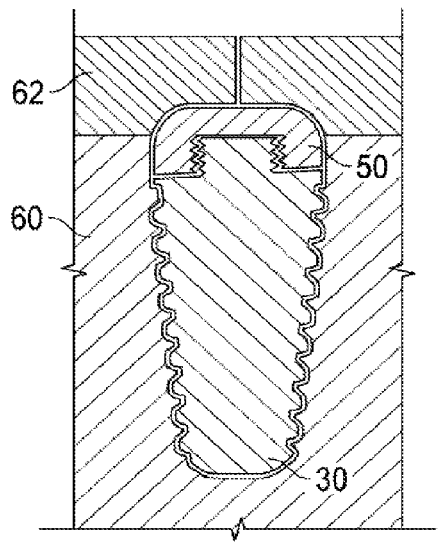
FIGS. 8A-8C are cross-sections of stages in an exemplary implantation according to certain aspects of this disclosure.
Figure 8B:
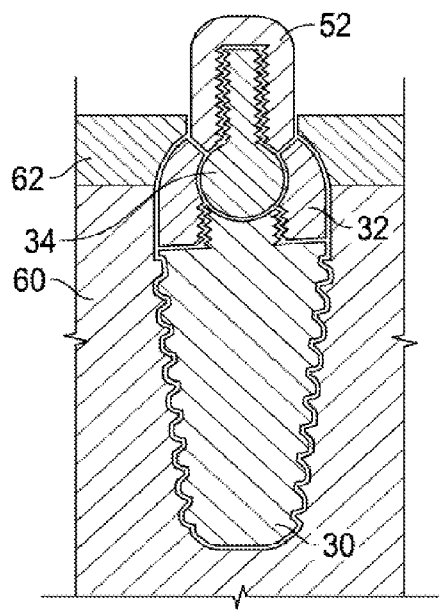
Figure 8C:
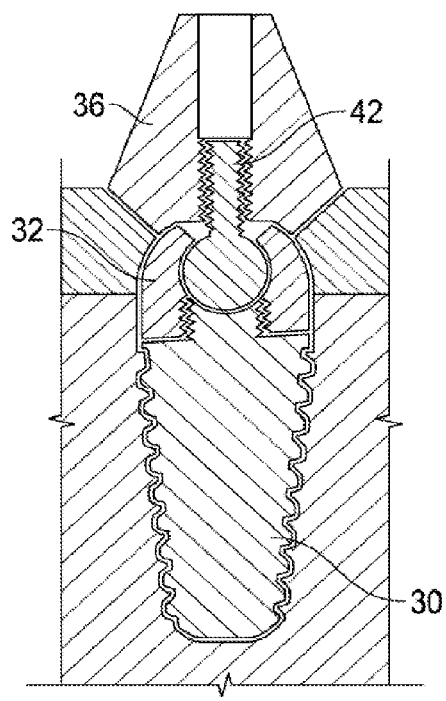

FIGS. 8A-8C are cross-sections of stages in an exemplary implantation process according to certain aspects of this disclosure. FIG. 8A shows the lower implant 30 placed through the gum tissue 62 and into the jaw bone 60 of a patient. In this embodiment, the lower implant 30 is oriented vertically under the location of the tooth to be replaced. It can be seen that, in this embodiment, the top of the lower implant 30 is recessed from the surface of the bone 60. In certain embodiments, the top of the lower implant 30 is flush with the surface of the bone 60. A healing cover 50 has been placed over the lower implant 30. In certain embodiments, the lower implant 30 comprises a first threaded portion and the healing cover 50 is configured to be removably coupled to the first threaded portion of the lower implant 32. In certain embodiments, the gum 62 is sutured over the healing cover 50.

In FIG. 8B, some gum tissue 62 and the healing cover 50 have been removed and an anchor 34 and upper implant 32 installed. The anchor is rotated to provide the desired angle of the tooth crown (not shown in FIG. 8B) that is to be attached. A healing cap 52 is installed over the threaded shaft 42. In certain embodiments, the step shown in FIG. 8B is omitted.

In FIG. 8C, the healing cap 52 has been removed and an abutment 36 has been coupled to the shaft 42. The lower spherical interface of the abutment 36, corresponding to the fourth substantially spherical surface 19 of the abutment 3 of FIG. 4B, mates with the top spherical surface of the upper implant 32, corresponding to the third substantially spherical surface 11 of the upper implant body 1 of FIG. 4B.

Figure 8D:
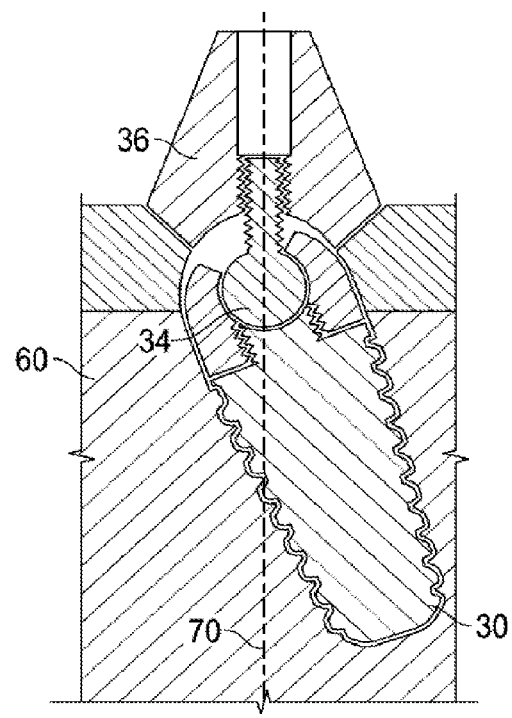
FIG. 8D is a cross-section illustrating an alternate implantation configuration according to certain aspects of this disclosure.

FIG. 8D is a cross-section illustrating another embodiment of an implantation configuration according to certain aspects of this disclosure. In this embodiment, the lower implant 30 has been implanted at an angle to a vertical axis 70 located under the location of the tooth to be replaced. This allows the lower implant 30 to be placed, for example, into a region of the jaw where the bone 60 is denser. It can be seen that the rotational capability of the anchor 34 relative to the lower implant 30 allows the abutment 36 to be placed in the same position as in FIG. 8C despite the difference in the position of the lower implant 30.

Figure 9A:
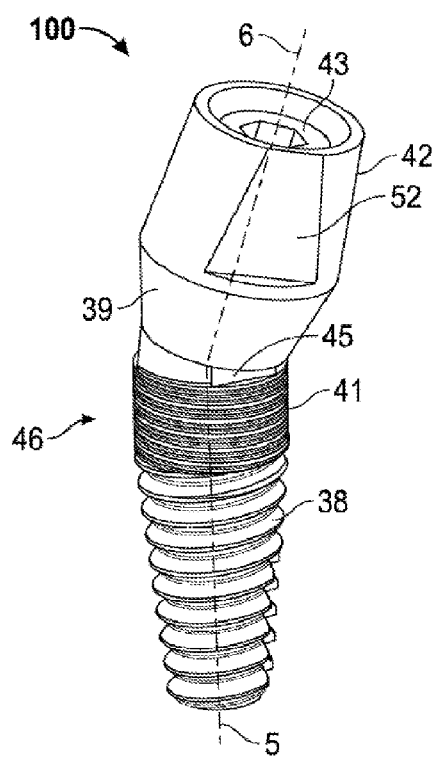
FIGS. 9A-9C illustrate another embodiment of a positionable dental implant according to certain aspects of this disclosure.
Figure 9B:
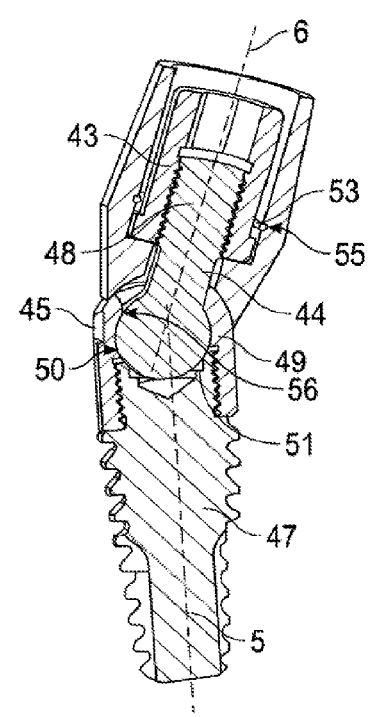
Figure 9C:
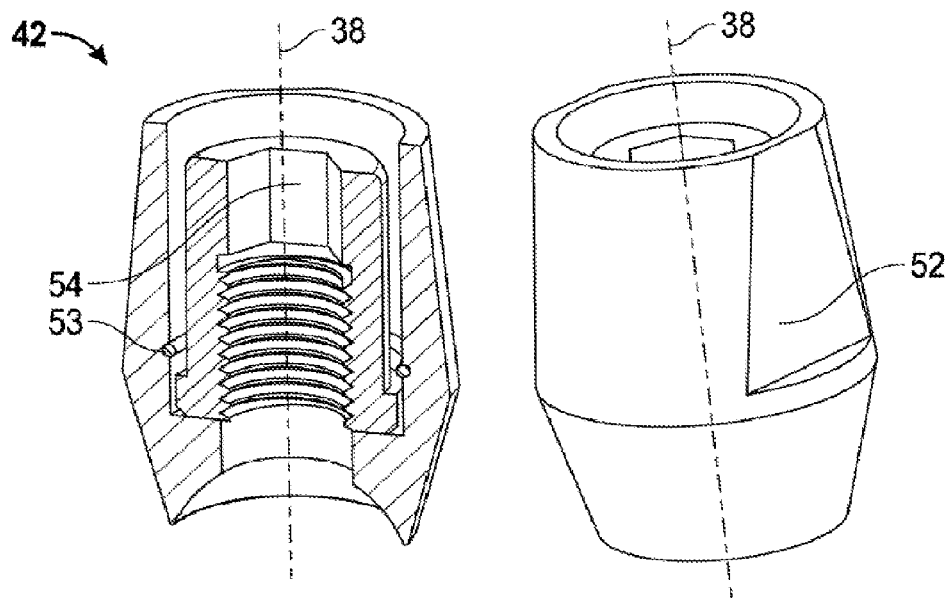

FIGS. 9A-9C illustrate another embodiment 100 of a positionable dental implant according to certain aspects of this disclosure. The following elements are identified in FIGS. 9A-9C.

| ref. identifier | Feature |
| --- | --- |
| 5 | axis of the lower implant body |
| 6 | axis of the abutment |
| 38 | Implant thread form |
| 39 | Reduced area of abutment |
| 41 | portion of upper implant body wherein the surface is abraded for osteoblast |
| 42 | Abutment |
| 43 | Captive nut |
| 44 | Anchor |
| 45 | upper implant scarf |
| 46 | Implant assembly (includes 44, 47, 49) |
| 47 | Lower implant body |
| 48 | shaft |
| 49 | Upper implant body |
| 50 | first substantially spherical surface |
| 51 | Flexure |
| 52 | abutment scarf |
| 53 | retaining clip |
| 54 | hexagonal recess |
| 55 | groove |
| 56 | second substantially spherical surface |
| 100 | dental implant |

In this embodiment, the abutment 42 comprises a captive locking nut 43 that is captured by a retaining clip 53 that engages a groove 55 formed in the abutment 42. In certain embodiments, the nut 43 comprises a hexagonal recess 54 that allows use of a tool (not shown) to tighten the nut 43 onto the shaft 44. Flexure 51 provides constant contact pressure between the first substantially spherical surface 50 of anchor 43 and the second substantially spherical surface 56.

Figure 10:
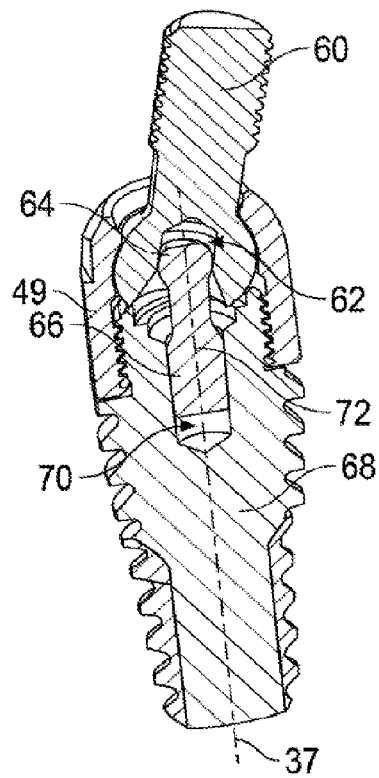
FIG. 10 depicts another embodiment of the implantable portion of a positionable dental implant according to certain aspects of this disclosure.

FIG. 10 depicts another embodiment of the implantable portion of a positionable dental implant 100 according to certain aspects of this disclosure. The following elements are identified in FIG. 10 in addition to elements previously identified.

60 Non-rotating anchor
62 anti-rotation cavity
64 Hex ball
66 anti-rotation post
68 Non-rotating lower implant body
70 Hex cavity
72 axis of anti-rotation post The anti-rotation post 66 comprises a hex ball 64 fits into the anti-rotation cavity 62 in the non-rotating anchor 60 such that the anchor 60 cannot rotate relative to the lower implant 68 about the axis 72 but can rotate about axes perpendicular to axis 72. In certain embodiments, the axis 72 is coincident with the centerline 37 of the lower implant body 68. The hex ball shaft 66 has a straight hex profile that matches the hex cavity 70 of lower implant 68 such that the anti-rotation post 66 cannot rotate relative to the lower implant body 68.

In certain embodiments, the hex ball 64 and anti-rotation cavity 62 each have six facets configured to engage each other. In certain embodiments, the facets of the hex ball 64 are curved about an axis perpendicular to axis 72. In certain embodiments, the hex ball 64 and anti-rotation cavity 62 have a common number of facets that is different from six.

Figure 11:
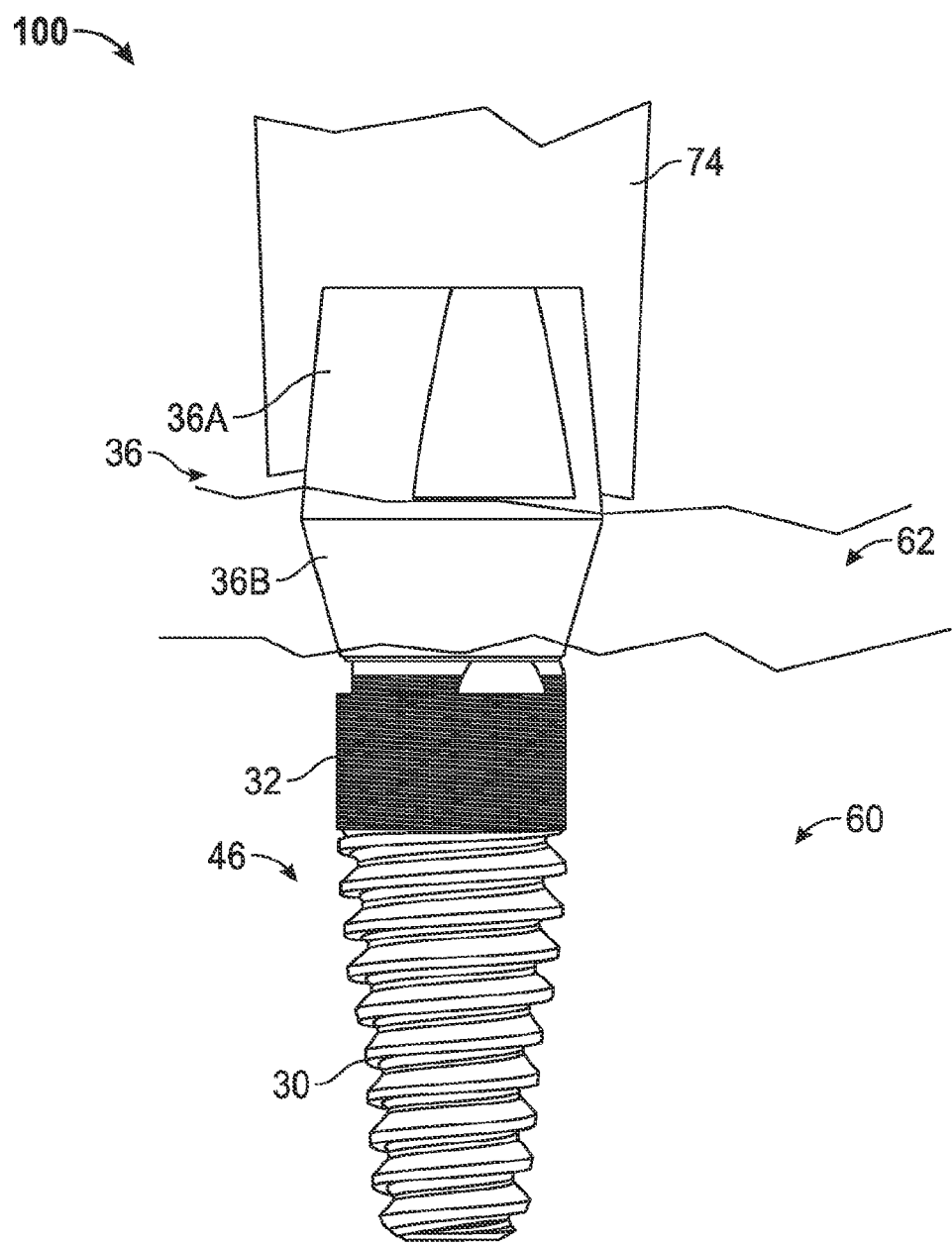
FIG. 11 depicts the positionable dental implant of FIG. 9A implanted in a patient's jaw according to certain aspects of this disclosure.

FIG. 11 depicts the positionable dental implant 100 of FIG. 9A implanted in a patient's jaw according to certain aspects of this disclosure. The upper portion 36A of the abutment 36 is configured to accept a crown 74. In certain embodiments, portion 36B is configured to be substantially embedded in the tissue 62 of the patient. In certain other embodiments, the implant assembly 46 is implanted at a greater depth, while in certain other embodiments, the implant assembly 46 is implanted at a lesser depth. In certain embodiments, the implant assembly 46 is implanted with the alpha axis 37 at an angle to the vertical (as seen in FIG. 11) similar to FIG. 8D. In certain embodiments, the elements of FIG. 10 replace the like elements of FIGS. 9A-9B.

Figure 12A:
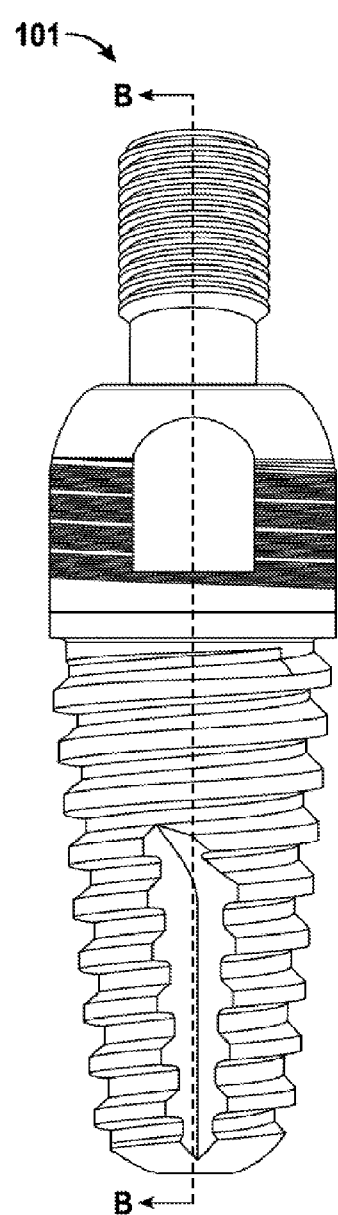
FIGS. 12A-12C depict another embodiment of a positionable dental implant according to certain aspects of this disclosure.
Figure 12B:
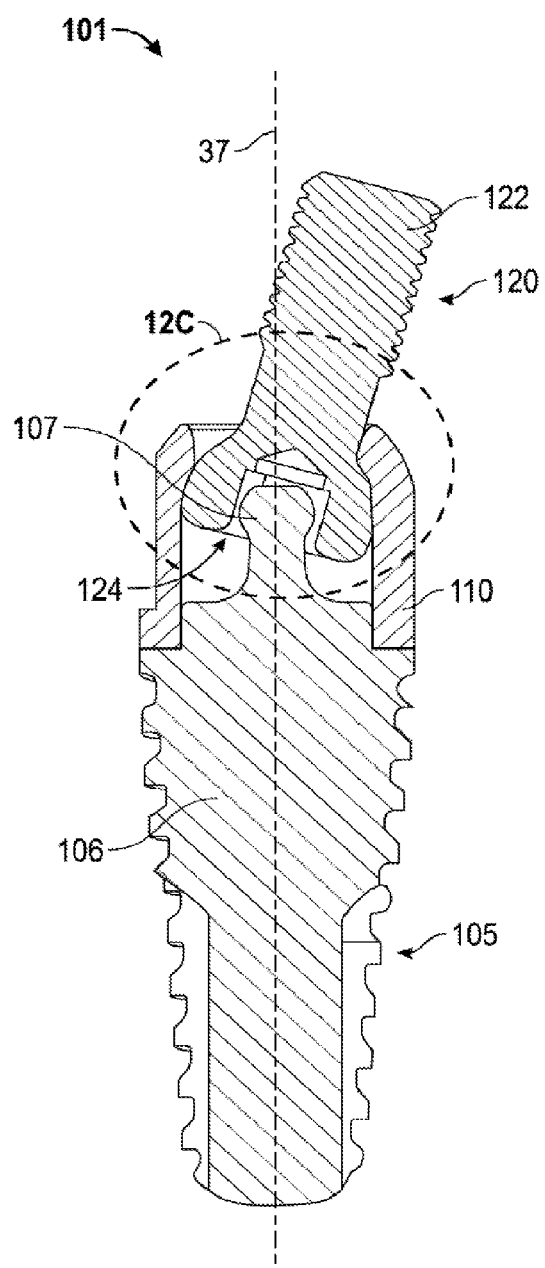
Figure 12C:
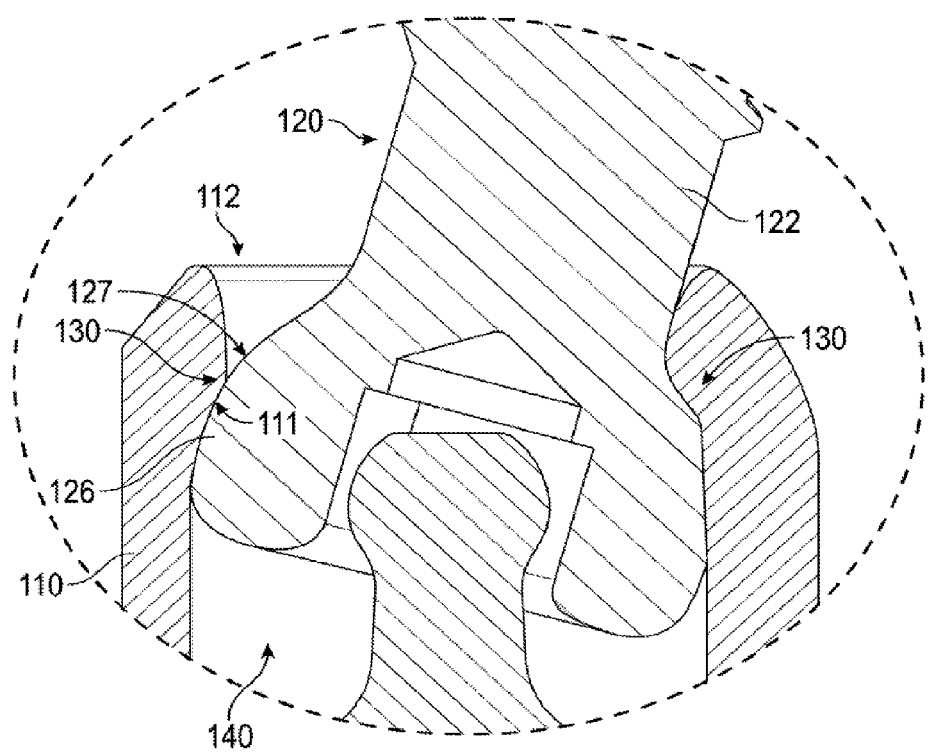

FIGS. 12A-12C depict another embodiment 101 of a positionable dental implant according to certain aspects of this disclosure. FIG. 12A depicts an external view of the assembled dental implant 101 with a section line B-B.

FIG. 12B is a cross-section along the section line B-B of FIG. 12A. Dental implant 101 includes a lower implant 105 having a body 106 and an anti-rotation post 107, an upper implant 110, and a positionable anchor 120 having a threaded shaft 122 and a base 126 with an anti-rotation cavity 124. In this embodiment, the upper implant 110 is electron-beam welded to the lower implant 105 prior to implantation in the patient's jaw. The area indicated by the broken-line circle labeled '12C' is enlarged in FIG. 12C.

FIG. 12C is an enlarged portion of FIG. 12B wherein the anchor 120 includes a base 126 having a spherical interface surface 127. Upper implant 110 has an internal interface 111 that is substantially spherical. When assembled, and after an abutment (not shown) is tightened onto the threaded body 122, the spherical interface surface 127 of the anchor 120 is in contact with the spherical interface surface 111 of the upper implant 110. This contact between surfaces 127 and 11 forms a continuous seal along a perimeter 130 around the edge of the opening 112 in the upper implant 110. This continuous seal resists debris and bacteria from entering the internal volume 140 formed within dental implant 100. Accumulation of debris, such as liquid or solid food, in a recess where bacteria can multiple and not be easily removed in normal oral care creates a risk of infection for the patient. Providing a continuous seal along perimeter 130 reduces this risk.

Figure 13A:
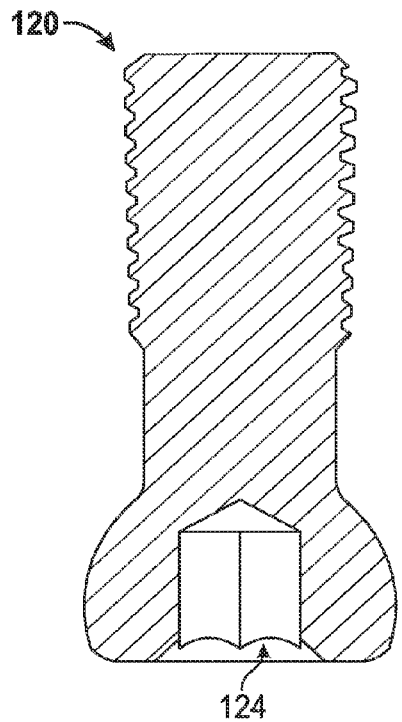
FIGS. 13A-13B depict details of the anchor of FIGS. 12A-12C according to certain aspects of this disclosure.
Figure 13B:
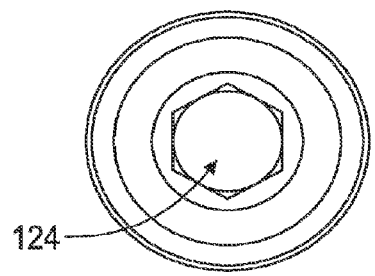

FIGS. 13A-13B depict details of the anchor of FIGS. 12A-12C according to certain aspects of this disclosure. FIG. 13A is a cross-section of the anchor 120 showing the anti-rotation cavity 124. FIG. 13B is an end view from the anti-rotation cavity 124 in which it can be seen that, in this embodiment, the cavity 124 has a hexagonal profile.

Figure 14A:
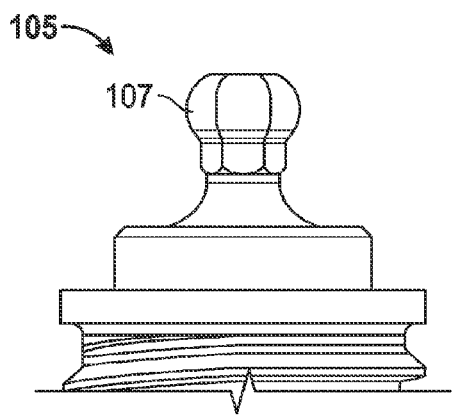
FIGS. 14A-14B depict details of the lower implant of FIGS. 12A-12C according to certain aspects of this disclosure.
Figure 14B:
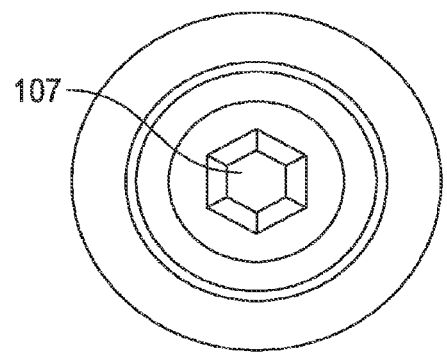

FIGS. 14A-14B depict details of the lower implant of FIGS. 12A-12C according to certain aspects of this disclosure. FIG. 14A is a cross-section of a portion of the lower implant 105 showing the anti-rotation post 107. FIG. 14B is an end view from the anti-rotation post 107 in which it can be seen that, in this embodiment, the post 107 has a hexagonal profile. In certain aspects, the dimensions of the post 107 and the cavity 124 are selected such that the post 107 has clearance within the cavity 124. In certain aspects, the post 107 and cavity 124 are fabricated such that there is effectively zero clearance, i.e. less than 0.001 inches, between the two when assembled.

When the dental implant 100 is assembled as shown in FIGS. 12A-12B, the hexagonal features of this embodiment of the post 107 are disposed within the hexagonal features of the this embodiment of the cavity 127. In this configuration, the anchor 120 is free to tilt with respect to the upper and lower implant 110, 105, i.e. rotate about axes that are perpendicular to the axis 101 shown in FIG. 12B. The hexagonal features of post 107 cooperate with the hexagonal features of the cavity 127 to resist rotation of anchor 120 relative to the upper and lower implant 110, 105 about the axis 101. In certain embodiments, the maximum dimension of an aspect the post 107, such as the width of the flats across the hexagon, and the minimum dimension of the corresponding aspect of the cavity 127 are selected to be identical to minimize the clearance between the post 107 and cavity 127.

Figure 15A:
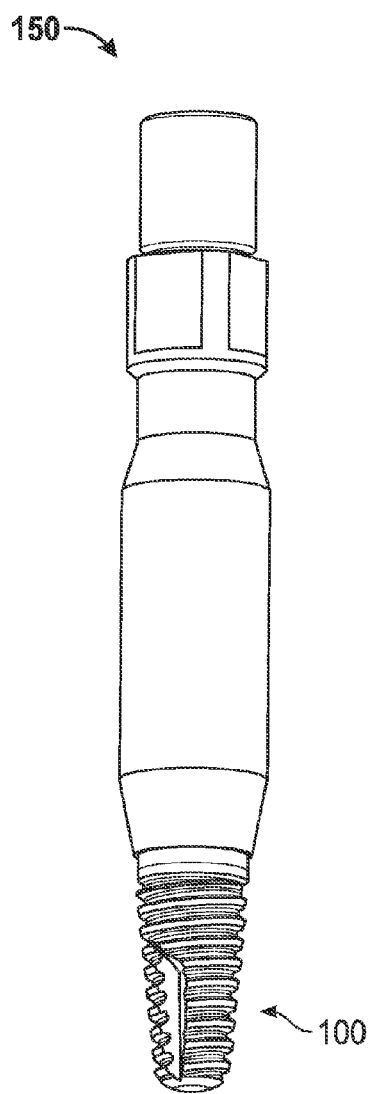
FIGS. 15A-15B depict perspective and cross-section views, respectively, of a T1 tool according to certain aspects of this disclosure.
Figure 15B:
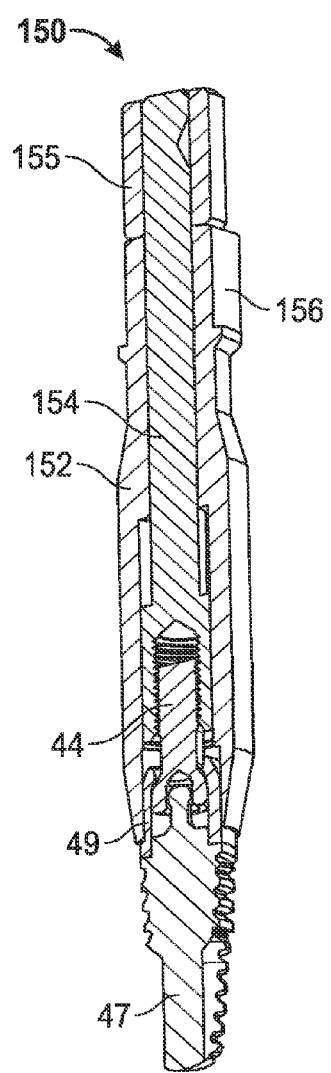

FIGS. 15A-15B depict perspective and cross-section views, respectively, of a T1 insertion tool 150 according to certain aspects of this disclosure. The tool 150 is adapted for installation of a dental implant 100, or similar, when the abutment 42 is not attached. The tool 150 comprises an outer tube 152 that is configured to engage the outer surface of the upper implant 49 and an inner shaft 154 that is configured to engage the shaft 48 of the anchor 44. Tightening the upper knob 155 pulls the anchor 44 upward against the inner surface 56 of the upper implant body 49 thereby locking the orientation of the tool 150 with respect to the lower implant body 47. Torque can then be applied to the flats 156 of the tool 150 to implant the lower implant 47 into the jawbone.

Figure 16A:
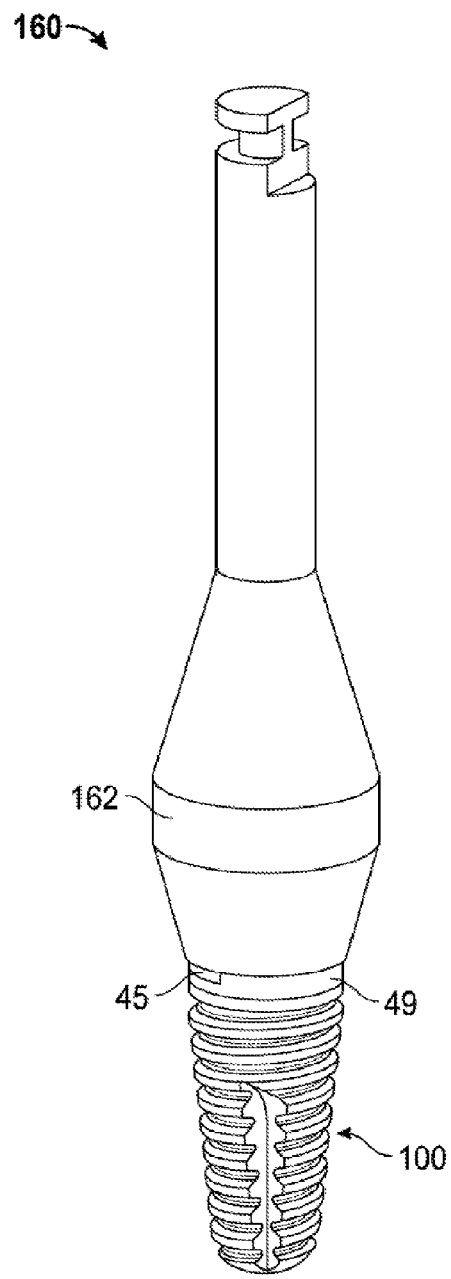
FIGS. 16A-16B depict perspective and cross-section views, respectively, of a T2 tool according to certain aspects of this disclosure.
Figure 16B:
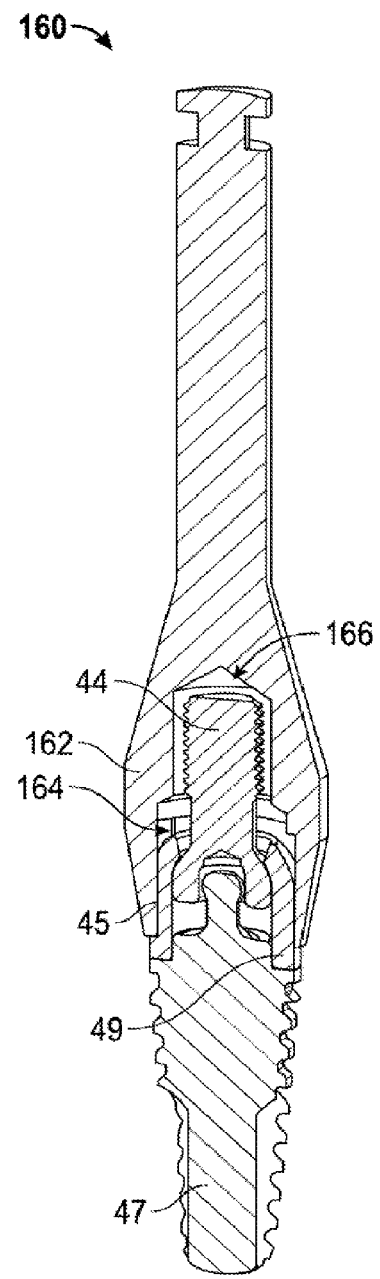

FIGS. 16A-16B depict perspective and cross-section views, respectively, of a T2 insertion tool 160 according to certain aspects of this disclosure. The tool 160 adapted for installation when the abutment 42 is not attached. The tool 160 comprises a shaft 162 having a first cavity that is configured to engage the upper implant body 49 and the upper implant scarf 45 such that the tool 160 can apply torque to the implant 100. In certain aspects, the implant 100 is free to fall out of the cavity 164. In certain aspects, a retention feature (not shown in FIG. 16A or 16B), for example an o-ring partially embedded in a wall of the cavity 164, provides retention force to retain the implant 100 within the cavity 164. A second cavity 166 provides space for the shaft 44 but does not engage the shaft 44.

Figure 17A:
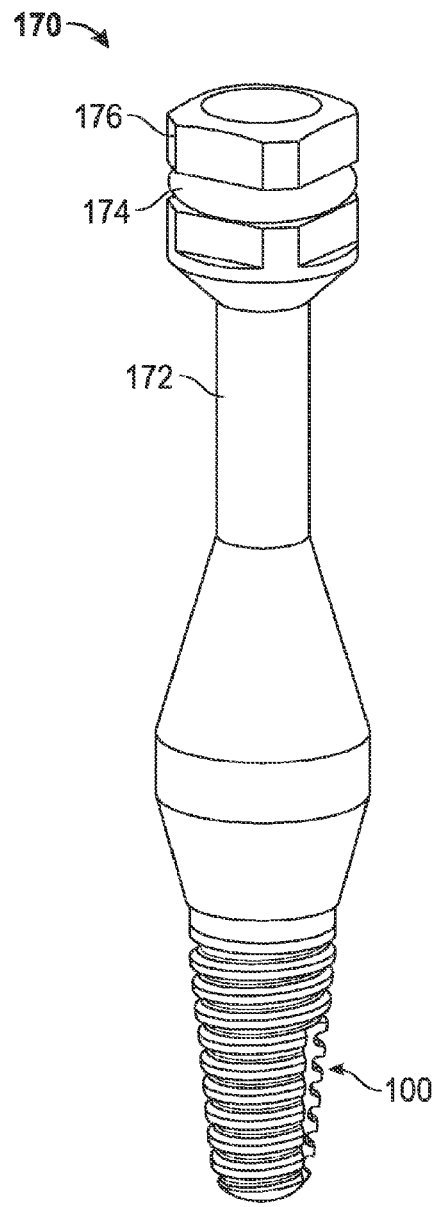
FIGS. 17A-17B depict perspective and cross-section views, respectively, of a T3 tool according to certain aspects of this disclosure.
Figure 17B:
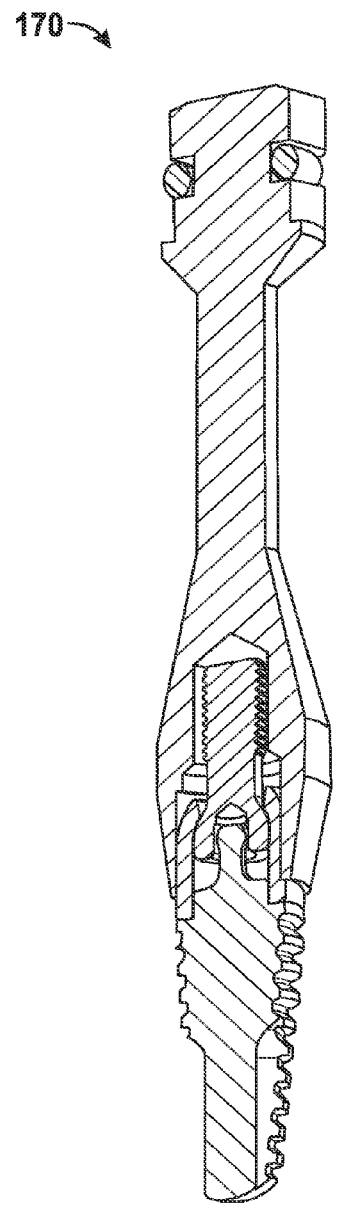

FIGS. 17A-17B depict perspective and cross-section views, respectively, of a T3 insertion tool 170 according to certain aspects of this disclosure. The tool 170 is adapted to engage the implant 100 in a manner similar to tool 160. Tool 170 comprises a series of torquing flats 176 and a retention feature 174, in this example an o-ring, to prevent the tool 170 from falling out of the device (not shown) applying torque to the torquing flats 176.

FIGS. 18A-18B depict perspective and cross-section views, respectively, of a T4 tool 180 according to certain aspects of this disclosure. The tool 180 is adapted for installation when the abutment 42 is attached and the captive nut 43 tightened. The tool 180 comprises a shaft 182 and a cavity 184 configured to engage the outside surface of the abutment 42 and the abutment scarf 52. In certain aspects, the implant 100 is free to fall out of the cavity 184.

Figure 19A:
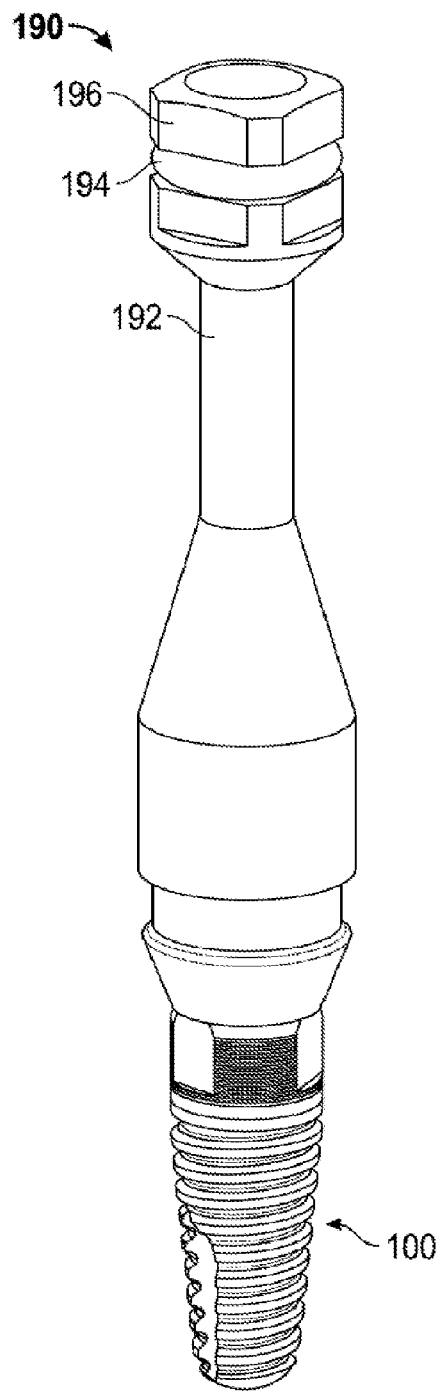
FIGS. 19A-19B depict perspective and cross-section views, respectively, of a T5 tool according to certain aspects of this disclosure.
Figure 19B:
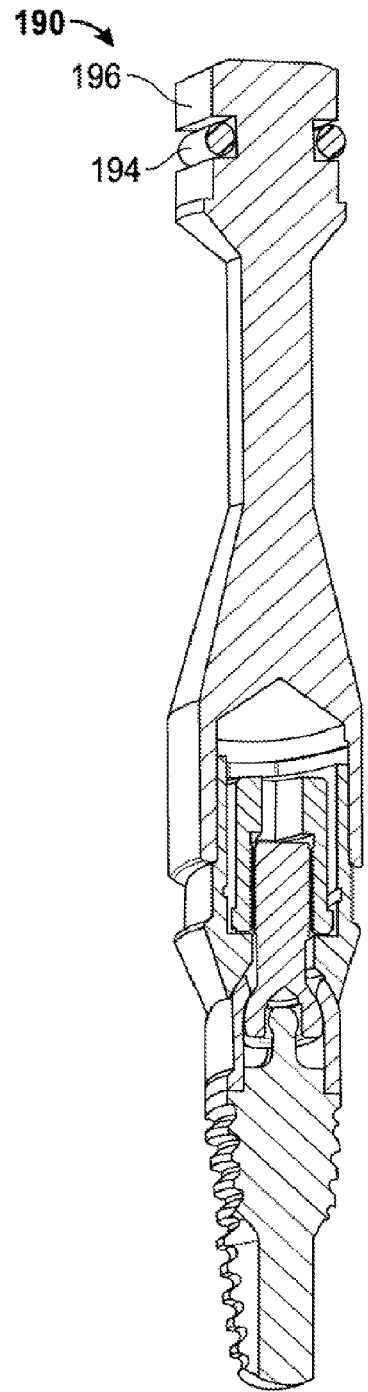

FIGS. 19A-19B depict perspective and cross-section views, respectively, of a T5 tool 190 according to certain aspects of this disclosure. The tool 190 is adapted to engage the implant 100 in a manner similar to tool 180. Tool 190 comprises a series of torquing flats 196 and a retention feature 194, in this example an o-ring, to prevent the tool 190 from falling out of the device (not shown) applying torque to the torquing flats 196.

Figure 20A:
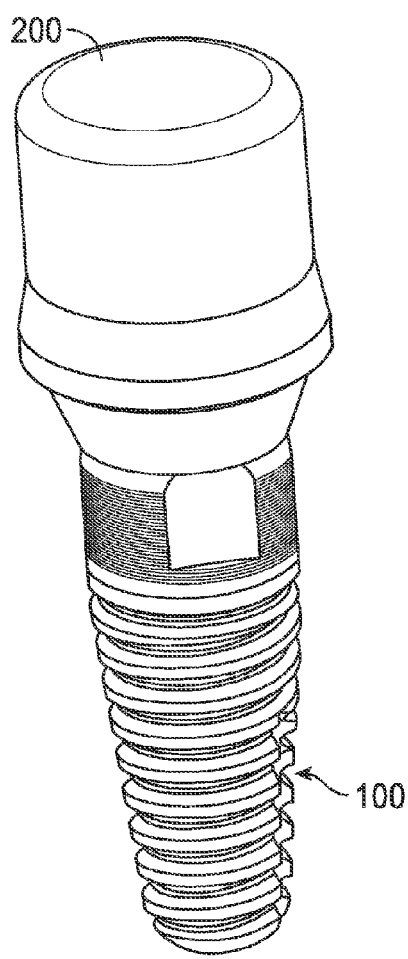
FIGS. 20A-20B depict perspective and cross-section views, respectively, of a healing cap according to certain aspects of this disclosure.
Figure 20B:
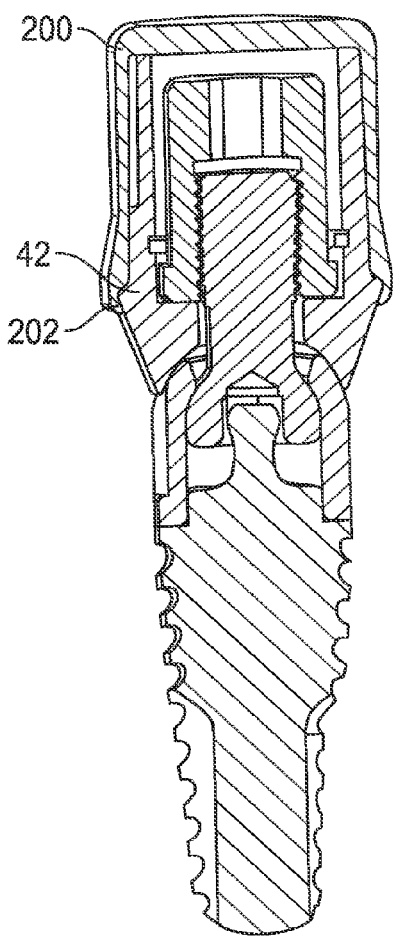

FIGS. 20A-20B depict perspective and cross-section views, respectively, of a healing cap 200 according to certain aspects of this disclosure. The cap 200 snaps onto an abutment 42 and rides against the top of the abutment 42. In certain embodiments, the cap 200 comprises a clip edge 202 configured to engage the ridge of the abutment 42.

Figure 21A:
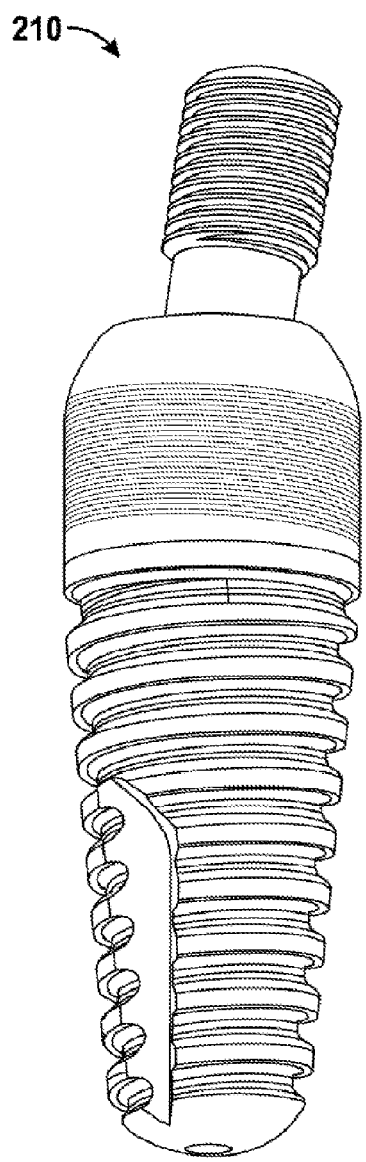
FIGS. 21A-21B depict perspective and cross-section views, respectively, of another embodiment of a positionable dental implant according to certain aspects of this disclosure.
Figure 21B:
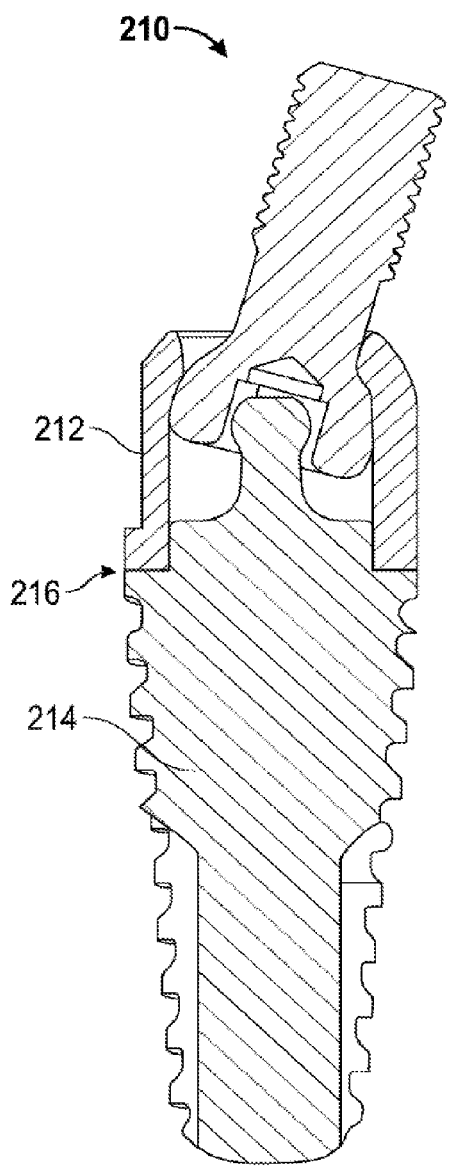

FIGS. 21A-21B depict perspective and cross-section views, respectively, of another embodiment of a positionable dental implant 210 according to certain aspects of this disclosure. In this embodiment, a upper implant body 212 and lower implant body 214 are configured similar to the upper and lower implant bodies 47 and 439 of implant 100, shown in FIG. 9A, except that upper and lower implant bodies 212 and 214 are welded along the seam 216. In certain aspects, the upper and lower implant bodies 212 and 214 are e-beam welded. In certain aspects, the upper and lower implant bodies 212 and 214 are continuously welded. In certain aspects, the upper and lower implant bodies 212 and 214 are intermittently welded.

The concepts disclosed herein provide a system and method for implantation of an implant body at an angle from a vertical axis under the location of a tooth to be replaced. The angular installation allows the implant body to be placed so as to improve the strength and healing of the dental implant in the jaw bone while retaining the ability to position the abutment, and therefore the crown, in the natural tooth orientation.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A dental implant system comprising:
an implant body comprising threads configured to engage bone, the implant body comprising a lower implant body, an upper implant body, and a post, the upper implant body coupled to the lower implant body with a first cavity between the upper implant body and the lower implant body, the implant body comprising an opening to the first cavity, the post coupled to the lower implant body such that the post cannot rotate relative to the lower implant body, the post projecting into the first cavity between the upper and lower implant bodies; and
an anchor extending through the opening into the first cavity, the anchor comprising a base having a second cavity, the base disposed at least partially within the first cavity with the post extending into the second cavity; and
wherein the post and second cavity are configured to cooperate so as to resist rotation of the anchor relative to the lower implant body about a centerline of the lower implant body while allowing rotation of the anchor relative to the lower implant body about axes perpendicular to the centerline.

2. The dental implant system of claim 1, wherein the base comprises a surface in contact with the upper implant body so as to form a continuous seal between the base and the upper implant body.

3. The dental implant system of claim 2, wherein the upper implant body defines the opening, the opening has a perimeter, and the base comprises a first substantially spherical surface that is in contact with the perimeter so as to form the continuous seal between the base and the upper implant body along the perimeter.

4. The dental implant system of claim 3, wherein the upper implant body further comprises an internal surface configured such that the first substantially spherical surface is at least partially in contact with the internal surface when the upper and lower implant bodies are coupled together with the base of the anchor disposed within the first cavity.

5. The dental implant system of claim 2, wherein the continuous seal between the base of the anchor and the upper implant body is maintained in all positions of the anchor relative to the upper implant body.

6. The dental implant system of claim 1, wherein the post comprises a hex ball, and the second cavity comprises a hex pocket.

7. The dental implant system of claim 1, further comprising an abutment configured to couple to the anchor.

8. The dental implant system of claim 7, wherein:
the upper implant body further comprises an external third substantially spherical surface; and
the abutment comprises a fourth substantially spherical surface configured such that the fourth substantially spherical surface is at least partially in contact with the third substantially spherical surface when the upper and lower implant bodies are coupled together with the base of the anchor disposed within the first cavity and the abutment coupled to a shaft of the anchor.

9. The dental implant system of claim 7, wherein the anchor comprises a threaded shaft, and the abutment comprises a nut configured to threadingly couple to the threaded shaft of the anchor.

10. The dental implant system of claim 1, wherein the lower implant body comprises a first threaded portion, and the upper implant body comprises a second threaded portion configured to be threadingly coupled to the first threaded portion.

11. The dental implant system of claim 10, wherein the dental implant system further comprises a healing cover configured to be removably coupled to the first threaded portion.

12. The dental implant system of claim 1, wherein the upper and lower implant bodies are configured to be welded together.

13. The dental implant system of claim 1, wherein the lower implant body comprises a hex cavity, the post comprises a hex profile that matches the hex cavity, and the post extends into the hex cavity of the lower implant body.

14. The dental implant system of claim 1, wherein a single monolithic piece comprises the post and the lower implant body.

15. The dental implant system of claim 1, further comprising an installation tool configured to be removably coupled to the upper implant body and apply a torque about the centerline of the lower implant body.

16. The dental implant system of claim 15, wherein the installation tool is further configured to be removably coupled to a shaft of the anchor.

17. The dental implant system of claim 7, further comprising an installation tool configured to be removably coupled to the abutment and apply a torque about the centerline of the lower implant body.

18. The dental implant system of claim 1, wherein the lower implant body extends within the upper implant body.

19. The dental implant system of claim 1, wherein the upper implant body completely surrounds the lower implant body along a portion of a length of the lower implant body.

20. A dental implant system comprising:
an implant body comprising a lower implant body, an upper implant body, and a post, the upper implant body comprising external threads, the upper implant body coupled to the lower implant body with a first cavity between the upper implant body and the lower implant body, the implant body comprising an opening to the first cavity, the post coupled to the lower implant body such that the post cannot rotate relative to the lower implant body, the post projecting into the cavity between the upper and lower implant bodies; and
an anchor extending through the opening into the first cavity, the anchor comprising a base having a second cavity, the base disposed at least partially within the first cavity with the post extending into the second cavity; and
wherein the post and second cavity are configured to cooperate so as to resist rotation of the anchor relative to the lower implant body about a centerline of the lower implant body while allowing rotation of the anchor relative to the lower implant body about axes perpendicular to the centerline.

21. The dental implant system of claim 20, wherein the base comprises a surface in contact with the upper implant body so as to form a continuous seal between the base and the upper implant body.

22. The dental implant system of claim 21, wherein the upper implant body defines the opening, the opening has a perimeter, and the base comprises a first substantially spherical surface that is in contact with the perimeter so as to form the continuous seal between the base and the upper implant body along the perimeter.

23. The dental implant system of claim 20, wherein the post comprises a hex ball, and the second cavity comprises a hex pocket.

24. The dental implant system of claim 20, further comprising an abutment configured to couple to the anchor.

25. The dental implant system of claim 24, wherein:
the upper implant body further comprises an external third substantially spherical surface; and
the abutment comprises a fourth substantially spherical surface configured such that the fourth substantially spherical surface is at least partially in contact with the third substantially spherical surface when the upper and lower implant bodies are coupled together with the base of the anchor disposed within the first cavity and the abutment coupled to a shaft of the anchor.

26. The dental implant system of claim 24, wherein the anchor comprises a threaded shaft, and the abutment comprises a nut configured to threadingly couple to the threaded shaft of the anchor.

27. The dental implant system of claim 20, wherein the lower implant body comprises a first threaded portion, and the upper implant body comprises a second threaded portion configured to be threadingly coupled to the first threaded portion.

28. The dental implant system of claim 27, wherein the dental implant system further comprises a healing cover configured to be removably coupled to the first threaded portion.

29. The dental implant system of claim 20, wherein the upper and lower implant bodies are welded together.

30. The dental implant system of claim 20, wherein the lower implant body comprises a hex cavity, the post comprises a hex profile that matches the hex cavity, and the post extends into the hex cavity of the lower implant body.

31. The dental implant system of claim 20, wherein a single monolithic piece comprises the post and the lower implant body.

32. The dental implant system of claim 20, further comprising an installation tool configured to be removably coupled to the upper implant body and apply a torque about the centerline of the lower implant body.

33. The dental implant system of claim 32, wherein the installation tool is further configured to be removably coupled to a shaft of the anchor.

34. The dental implant system of claim 24, further comprising an installation tool configured to be removably coupled to the abutment and apply a torque about the centerline of the lower implant body.

35. The dental implant system of claim 20, wherein the lower implant body extends within the upper implant body.

36. The dental implant system of claim 20, wherein the upper implant body completely surrounds the lower implant body along a portion of a length of the lower implant body.

* * * * *